(12) United States Patent
Hennessy et al.

(10) Patent No.: US 6,277,071 B1
(45) Date of Patent: Aug. 21, 2001

(54) CHRONIC DISEASE MONITOR

(75) Inventors: Gary R. Hennessy, Avon; Ronald F. Larity, Somers, both of CT (US)

(73) Assignee: Delphi Health Systems, Inc., Windsor, CT (US)

( * ) Notice: Subject to any disclaimer, the term of this patent is extended or adjusted under 35 U.S.C. 154(b) by 0 days.

(21) Appl. No.: 09/340,211

(22) Filed: Jun. 25, 1999

(51) Int. Cl.[7] .................................................. A61B 5/00
(52) U.S. Cl. ............................................................ 600/300
(58) Field of Search ............................................ 600/300

(56) References Cited

U.S. PATENT DOCUMENTS

| | | |
|---|---|---|
| 4,731,725 | 3/1988 | Suto et al. . |
| 4,731,726 | 3/1988 | Allen, III . |
| 4,733,354 | 3/1988 | Potter et al. . |
| 4,803,625 | 2/1989 | Fu et al. . |
| 4,945,476 | 7/1990 | Bodick et al. . |
| 5,191,524 | 3/1993 | Pincus et al. . |
| 5,251,126 | 10/1993 | Kahn et al. . |
| 5,255,187 | 10/1993 | Sorenson . |
| 5,307,263 | 4/1994 | Brown . |
| 5,404,292 | 4/1995 | Hendrickson . |
| 5,473,537 | 12/1995 | Glazer et al. . |
| 5,517,405 | 5/1996 | McAndrew et al. . |
| 5,642,731 | 7/1997 | Kehr . |
| 5,672,154 | 9/1997 | Sillen et al. . |
| 5,779,634 | 7/1998 | Ema et al. . |
| 5,802,494 | 9/1998 | Kuno . |
| 5,846,189 | 12/1998 | Pincus . |
| 5,878,746 | 3/1999 | Lemelson et al. . |

OTHER PUBLICATIONS

Diabetes Management System product advertisment, "Diabetes Educator", May–Jun. 1999.
CliniPro™ by NuMedics, product brochure, Jun. 1997.
Diabetes Population Health Management by Control Diabetes Services, Inc., product brochures, 1998.

*Primary Examiner*—John P. Lacyk
(74) *Attorney, Agent, or Firm*—Brown Raysman Millstein Felder & Steiner LLP

(57) ABSTRACT

A system for monitoring a chronic disease is disclosed. The monitor includes a database for storing a plurality of patient data entries and sorts the patient data entries according to whether a test threshold is crossed. Each of the patient data entries includes personal information of a patient and a set of guidelines concerning the patient's care. The guideline represents a plurality of rules concerning a patient's care derived from accepted tests used to monitor the disease represented in an algorithm. A processor separates the patient entries designated by the user according to the test thresholds, such as for HbA1c, lipids, liver enzyme and microalbumin, for the disease of diabetes. If the test threshold value derived from the guideline is crossed, an alert sequence is activated, in which the patient is categorized as a high risk patient, the physician is notified, the patient is notified, the health care provider is notified, and the patient's treatment plan is altered to treat the high risk patient.

19 Claims, 26 Drawing Sheets

| Complications | | |
|---|---|---|
| Type | Present | |
| Retinopathy | ☐ | |
| Neuropathy | ☐ | |
| Nephropathy | ☐ | |
| PVD | ☐ | |
| CAD | ☐ | |
| Cerebro Vascular | ☐ | |

Help  Out

| Current Therapy plan | LastName3, FirstName3 | Registry ID:032-66-7543 | ☐ ☒ |
|---|---|---|---|

Provider: Williams, William G  
Last Changed On: 6/10/99

Therapy Plan Comments

| Date | Comment |
|---|---|
| 6/10/99 | added Lipitor based on last test results |

Medications

| Type | Medication | Dosage | Frequency | Start Date |
|---|---|---|---|---|
| Oral Agents | Metformin (Glucophage) | 500mg | bid | 3/3/98 |
| Other Meds | Atorvastatin(Lipitor) | 10mg | qd | 6/10/99 |

Nutrition Plan Summary  [Detail]

Exercise Plan Summary  [Detail]

[Help]  [Change Therapy]  [History]  [Out]

| Provider Information | | Williams, William G | | Provider ID:23-1345-4444 | |
|---|---|---|---|---|---|
| Profile | | Provider Detail | | Patient List | |

Alerts (14 Active Alerts) for Patient of Williams, William G

| Patient | Date | Test Type | Detail |
|---|---|---|---|
| LastName3, FirstName3 | 3/1/98 | HbA1c | Goal 7.0 , Threshold 9.5 , Result 12.0 |
| LastName2, FirstName2 | 3/2/98 | HbA1c | Goal 7.0 , Threshold 9.5 , Result 9.9 |
| LastName3, FirstName3 | 3/4/98 | Lipids (LDL) | Goal 130 , Threshold 160 , Result 175 |
| LastName3, FirstName3 | 3/4/98 | Lipids (LDL) | Goal 130 , Threshold 160 , Result 175 |
| LastName2, FirstName2 | 3/12/98 | HbA1c | Goal 7.0 , Threshold 9.5 , Result 167 |
| LastName3, FirstName3 | 6/5/98 | HbA1c | Goal 7.0 , Threshold 9.5 , Result 11.4 |
| LastName2, FirstName2 | 6/5/98 | HbA1c | Goal 7.0 , Threshold 9.5 , Result 10.2 |
| LastName3, FirstName3 | 6/6/98 | Lipids (LDL) | Goal 130 , Threshold 160 , Result 165 |
| LastName3, FirstName3 | 6/6/98 | Lipids (LDL) | Goal 130 , Threshold 160 , Result 165 |
| LastName3, FirstName3 | 9/5/98 | HbA1c | Goal 7.0 , Threshold 9.5 , Result 10.7 |

Review All

Reminders (1 Active Reminder) directed to Williams, William G

| Created | Schedule | Patient | Author | Subject |
|---|---|---|---|---|
| 4/29/99 | Next Visit | Sample3, AnthemBCBSComp | Williams, William G | Smoking cessation program |

Review All

| Help | | HEDIS99 | Print Provider | Quality Summary | Out |
|---|---|---|---|---|---|

*FIG. 15*

Quality Report – All Patients

Patient Population

| Category | Patients | Percentage |
|---|---|---|
| Type 1 | 9 | 3.9 |
| Type 2 | 221 | 96.1 |
| Gestational | | |
| All Patients | 230 | 100.0 |

HbA1c Tests

| Category | Patients Tested | Percent Tested | Average Value |
|---|---|---|---|
| Type 1 | 2 | 22.2 | 9.9 |
| Type 2 | 79 | 35.7 | 7.5 |
| Gestational | | | |
| All Patients | 81 | 35.2 | 7.5 |

Eye Exams

| Category | Patients Tested | Percent Tested |
|---|---|---|
| Type 1 | 2 | 22.2 |
| Type 2 | 77 | 34.8 |
| Gestational | | |
| All Patients | 79 | 34.3 |

FIG. 17

Quality Report — Provider: LastName6, FirstName6

Patient Population

| Category | Patients | Percentage |
|---|---|---|
| Type 1 | | |
| Type 2 | 21 | 100.0 |
| Gestational | | |
| All Patients | 21 | 100.0 |

HbA1c Tests

| Category | Patients Tested | Percent Tested | Average Value |
|---|---|---|---|
| Type 1 | | | |
| Type 2 | 5 | 23.8 | 6.6 |
| Gestational | | | |
| All Patients | 5 | 23.8 | 6.6 |

Eye Exams

| Category | Patients Tested | Percent Tested |
|---|---|---|
| Type 1 | | |
| Type 2 | 5 | 23.8 |
| Gestational | | |
| All Patients | 5 | 23.8 |

Help    Print    Out

*FIG. 19*

| Warning Symptoms and Signs of Diabetic Foot Problems | | |
|---|---|---|
| | Symptoms | Signs |
| Vascular | Cold Feet<br>Intermittent claudication involving calf or foot<br>Pain at rest, especially nocturnal, relieved by dependency | Absent pedal, popliteal, or femoral pulses<br>Femoral bruits<br>Dependent rubor, plantar pallor on elevation<br>Prolonged capillary filling time (>3-4 sec)<br>Decreased skin temperature |
| Neurologic | Sensory: burning, tingling, or crawling sensations; pain and hypersensitivity, cold feet<br>Motor: weakness (foot drop)<br>Autonomic: diminished sweating | Sensory: deficits (vibratory and proprioceptive, then pain and temperature perception), hyperesthesia<br>Motor: diminished to absent deep tendon reflexes (Achilles, then patellar), weakness, sweating<br>Autonomic: diminished to absent sweating |
| Musculoskeletal | Gradual change in foot shape, sudden painless change in foot shape, with swelling, without history or trauma | Cavus feet with claw toes<br>Drop foot<br>"rocker-bottom" foot<br>(Charcot's joint)<br>Neuropathic arthropathy |
| Dermatologic | Exquisitely painful or painless wounds<br>Slow-healing or nonhealing wounds or necrosis<br>Skin color changes (cyanosis, redness)<br>Chronic scaling, itching or dry feet<br>Recurrent infections (e.g., paronychia, athlete's foot) | Skin: Abnormal dryness<br>Chronic tinea infections<br>Keratotic lesions with or without hemorrhage (plantar or digital)<br>Trophic ulcer<br>Hair: Diminished or absent<br>Nails: Trophic changes<br>Onychomycosis |

FIG. 20

Review Patient History — LastName3, FirstName3 — Registry ID: 032-66-7543

Display

- ☑ HbA1c
- ☑ Eye Exam
- ☑ Lipids
- ☑ Microalbumin
- ☑ Liver Enzyme
- ☑ Quality Guideline
- ☑ Quality Plan
- ☑ Provider
- ☑ Therapy
- ☑ Office Visit
- ☑ Note
- ☑ Reminder
- ☑ Patient Communication
- ☑ Patient Services
- ☑ Meter

[Select All] [Clear All] [Refresh Display]

Summary

| Date | Event | | Detail |
|---|---|---|---|
| 6/21/99 | HbA1c | Alert | Goal 7.0 , Threshold 9.5 , Result 10.2 |
| 6/19/99 | HbA1c | Alert | Goal 7.0 , Threshold 9.5 , Result 11.0 |
| 6/10/99 | HbA1c | | Goal 7.0 , Threshold 9.5 , Result 9.0 |
| 6/10/99 | Therapy | | Changed Insulin: None Oral: Metformin (Glucophage) Other: Atorvastatin (Lipitor) |
| 4/29/99 | Reminder | | Author: Williams, William G , Subject: Smoking cessation program |
| 3/13/99 | Office Visit | | BP 165/95 , Wt 246 , Provider: Williams, William G |
| 3/13/99 | Foot Exam | | PVD |
| 3/4/99 | HbA1c | | Goal 7.0 , Threshold 9.5 , Result 9.4 |
| 2/12/99 | Liver Enzyme | | ALT 10 , AST 30 |
| 12/15/98 | Office Visit | | BP 178/93 , Wt 251 , Provider: Williams, William G |
| 12/15/98 | Foot Exam | | PVD |
| 12/5/98 | HbA1c | Alert | Goal 7.0 , Threshold 9.5 , Result 9.7 |
| 12/4/98 | Lipids | | LDL (Goal 130 , Threshold 160 , Result 158) , HDL 62 , Total 254 , Triglyceride |
| 9/5/98 | Therapy | | Changed Insulin: Humulin Oral: Metformin (Glucophage) Other: |
| 9/5/98 | HbA1c | Alert | Goal 7.0 , Threshold 9.5 , Result 10.7 |
| 9/4/98 | Lipids | | LDL (Goal 130 , Threshold 160 , Result 155) , HDL 60 , Total 287 , Triglyceride |

[Help] [Print] [Out]

*FIG. 21*

CHRONIC DISEASE MONITOR

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

This invention relates generally to data processing systems. More specifically, this invention relates to a new and improved apparatus and method for managing chronic disease which allows multiple access to patient data by medical providers, pay organizations and/or the patient. Chronic disease data is generated through the input and creation of a chronic disease model(s), patient history, a patient treatment plan, provider parameters, tests, expected and measured outcomes, and associated data. An integrated chronic disease monitor capable of providing communication between medical providers, pay organizations and the patient is provided. The chronic disease monitor automatically plans events (clinical exams and patient services) and generates alerts to the medical provider, pay provider and patient, if a test is not performed as planned, and also if the test results do not fall within an expected range.

2. Description of the Related Art

The concept of cost containment and efficiency of medical care services, commonly known as managed care, has taken on significant importance in the health care industry. Pay providers, in the form of employers, government agencies, insurance companies, health care maintenance organizations, and the like, frequently set forth a series of thresholds which must be established before a patient may have covered access to medical services. Communication of the patient's etiology, treatment plan and updating any changes thereto, is tremendously cumbersome, requiring countless hours by medical providers and their staff to insure this information is organized and accurately communicated to the pay provider, as well as the patient, so that the patient may access covered services and optimize treatment. Further, it is often difficult for the medical provider and/or pay provider to measure the success of the services rendered to the patient and/or the patient's own follow up with the treatment plan.

Certain chronic diseases, such as diabetes, have known etiologies and associated risk factors. Guidelines for treatment have been promulgated by, e.g. the American Diabetes Association, the National Commission for Quality Assurance (NCQA) and Diabetes Quality Improvement Project (DQUIP). These guidelines incorporate known complications associated with diabetes such as retinopathy, neuropathy, nephropathy, Pulmonary Vascular Disease (PVD), Cardial Artery Disease (CAD) and cerebral vascular disease. In addition to various tests associated with monitoring the diabetes, such as HbAlc (measuring glycosolated hemoglobin levels), microalbumin (blood protein), lipids (cholesterol), etc., the physician must typically perform routine eye and foot examinations to monitor the progress of the disease. These tests are in conjunction with those examinations normally associated with an office visit, i.e. blood pressure, temperature, weight, pulse, etc. In addition, there is a significant education and behavior component to the treatment of the disease which can encompass such items as nutrition counseling, smoking cessation, and self education about the disease. The Center for Disease Control estimates that diabetes is reaching epidemic proportions in the United States. Effective treatment centers on the known parameters and risk factors associated with the disease, and insuring that the patient is meeting the objectives of the treatment plan.

The patient's ability to self monitor blood glucose values at home has significantly improved the ability of the patient (and medical provider) to control the progress of the disease. Hand held monitoring units, such as disclosed in U.S. Pat. No. 4,731,726 to Allen, III, allow the patient to have a portable monitor which generates test values for the blood glucose level and stores the test results. The data may then be downloaded and/or transferred to a computer. The monitor may generate a recommendation to the patient based on patient data, physician input data and test results, such as an increased insulin dosage. U.S. Pat. No. 5,251,126 to Kahn et al illustrates another diabetes data analysis and interpretation method which identifies insulin intake regimens and identifies statistically significant changes in blood glucose levels in relationship to the insulin levels.

The use of computers to generate a patient record registry and to record data associated with the treatment of those patients enhances the provider's ability to assess the patient's health and generate an assessment plan. U.S. Pat. No. 5,262,943 to Thibado et al discloses a system which receives standardized test data as well as a therapists's subjective evaluations to generate an assessment report for the care of an individual in the mental health field. U.S. Pat. No. 5,265,010 to Evans-Paginelli discloses a hospital patient document method and apparatus which is used to generate an initial patient health care plan, identifying the patient's problems, expected outcomes and interventions to achieve those outcomes.

The use of statistical analysis to create a diagnostic model for a given disease has been employed to create trained neural networks. U.S. Pat. No. 5,769,074 to Barnhill et al, discloses a computer based method which employs the steps of collecting data about patients (such as biological, physical, demographic, racial, environmental); digitizing the data and medical historical data; selecting digitized values that are associated with the diagnosis of a disease; scaling the data; performing tests to analyze the discriminating power of the data; grouping individual data values; preprocessing the data; inputting selected data to make preprocessed values into a computer based neural network in order to train the neural network; analyzing the contributions of the individual data inputs to the network; selecting the optimally trained neural network based on the performance, accuracy and cost; and inputting other patient data into the neural network to produce an output value which indicates whether the patient may have or be susceptible to the disease. Such technology has application to diagnostic patterns which are too subtle or too complex for humans and conventional computational methods to identify and allow for the provider to access large neural networks which are capable of recognizing diagnostic patterns. U.S. Pat. No. 5,860,917 to Comanor, et al, discloses such a neural network with a statistical model derived using a robustified similarity metrical least squares (SMILES) analysis.

In contrast to the neural network developed through statistical analysis of patient data and risk factors to create a diagnostic protocol, certain chronic diseases, such as diabetes, have a known and highly defined treatment protocol. Though incurable, the risk factors associated with diabetes and the complications of diabetes have been well studied. The diabetic patient, however, must be closely monitored to control the disease. It is estimated, however, that physicians associated with the treatment of diabetes do not use computer based data systems to manage and maintain their files with respect to the diabetic patient. Indeed, it is estimated that less than ten percent (10%) of all physicians use computers in the treatment of their patients for purposes other than billing.

According to the Center for Disease Control (CDC), advances in diabetes research now provide the clinical and therapeutic means to improve outcomes for people with diabetes. The 1993 landmark study, the Diabetes Control and Complications Trial (DCCT), conclusively showed that improved glucose control can retard the onset and progression of diabetes complications affecting the eyes, kidneys, and nerves. A second study in the United Kingdom, entitled United Kingdom Prospective Diabetes Study (UKPDS), released in 1998, confirmed the results of the DCCT and left little doubt about the benefit of lowering blood glucose levels as close to normal as possible. In addition, new medications are available to lower blood glucose and methods for improving glucose levels have greatly improved. The key factor in accomplishing improved results is being able to support the delivery of care that is based on achieving these clear and critical goals.

For providers of diabetes care, these two recently completed studies have now established that there is great personal and economic benefit for diabetic patients to reduce and maintain blood glucose levels as close to normal as possible. For people with Type 2 diabetes, who constitute 90–95% of all diabetic patients, (ADA), aggressive reduction and control of blood glucose levels reduces the risk of blindness and kidney failure by 25%. For patients who also have high blood pressure and aggressively reduce it, major reductions in risk of stroke (44%) and heart failure (56%) can be achieved. (UKPDS Preliminary Results 1998).

With the scientific basis supporting the need for as close to normal blood glucose control now established, the opportunity to improve results begins in an environment that currently falls far short of this goal. The need for great improvement in diabetes care is evidenced by the following assessment from CDC: "Nonetheless, research advances in diabetes are not being communicated effectively and diabetes is not being managed aggressively. The U.S. is far from reaching the objectives set in the U.S. Department of Health and Human Services' Healthy People 2000. Physician practices often do not meet recommended standards of diabetes care. Many patients do not manage their diabetes well. Furthermore, the health care system, which is designed to treat acute and episodic illnesses, is poorly equipped to manage a complex, multi systemic chronic disease like diabetes . . . "

HEDIS (Health Plan Employer Data and Information Set) serves as the clinical performance measurement and data repository for private and federal health-care buyers. HEDIS is a database of quality measures developed by NCQA and used as a standard evaluation tool for health plans. National quality reporting has established that the patient eye exam, the initial and single standard quality measure for diabetes, is still not completed each year for more than half of all patients. Without tools to plan for the care and to collect and monitor data, diabetes care providers continue to struggle to improve their performance with this single basic measure.

Thus, what is needed is a data processing system and method for managing diabetes care where utilizes known medical standards adopted by the American Diabetes Association, among others, to customize a treatment plan, which can interface with the physician, health care plan and patient, and defines a set of criteria which defines a high risk patient and which continually monitors the patient, setting forth alarms when the patient fails receive a planned examination or service and/or the examination does not fall within an expected range.

SUMMARY OF THE INVENTION

The above-discussed and other drawbacks and deficiencies of the prior art are over come or alleviated by the chronic disease monitor of the present invention.

According to the present invention there is provided a system for monitoring a chronic disease including a database for storing a plurality of patient data entries. Each of the patient data entries includes personal information of a patient and a set of guidelines concerning the patient's care. A user interface is included for displaying the patient data entries stored in the database and entering the patient entries for storage in the database. A processor retrieves the patient data entries selected by the user interface from the data base and stores the patient data entries in accordance to an algorithm. The algorithm comprises a plurality of rules for comparing patient data entries to the guideline to determine whether a test threshold has been exceeded The processor separates the patient entries designated by the user according to a test threshold stored in said guideline. The test thresholds represent known parameters associated with the chronic disease, such as blood glucose, lipids, liver enzyme and microalbumin for the disease of diabetes. If the test threshold value derived from the guideline is exceeded, an alert sequence is activated, in which the patient is categorized as a high risk patient, the physician is notified, the patient is notified, the health care provider is notified, and the patient's treatment plan is altered to treat the high risk patient.

In a preferred embodiment, test values from a meter device or offsite laboratory are electronically transferred to the monitor.

BRIEF DESCRIPTION OF THE DRAWINGS

FIG. 3 is a graphical window displayed to a user entering a patient record;

FIG. 4 is another graphical window displayed to a user entering a patient record for complications;

FIG. 5 is another graphical window displayed to a user entering a patient record for office visits;

FIG. 6 is another graphical window displayed to a user entering a patient record for a patient quality plan;

FIG. 7 is another graphical window displayed to a user entering a patient record for a patient therapy plan;

FIG. 8 is a graphical window displayed to a user entering a provider record;

FIG. 15 is another graphical window displayed to a user entering a risk manager record;

FIG. 17 is a graphical window displayed to a user entering a quality report;

FIG. 19 is a graphical window displayed to a user entering a quality report by provider;

FIG. 20 is a graphical window displayed to a user illustrating warning symptoms and signs for diabetic foot problems; and FIG. 21 is a graphical window displayed to a user entering a patient history record.

DETAILED DESCRIPTION OF THE PREFERRED EMBODIMENT

Figure 1:
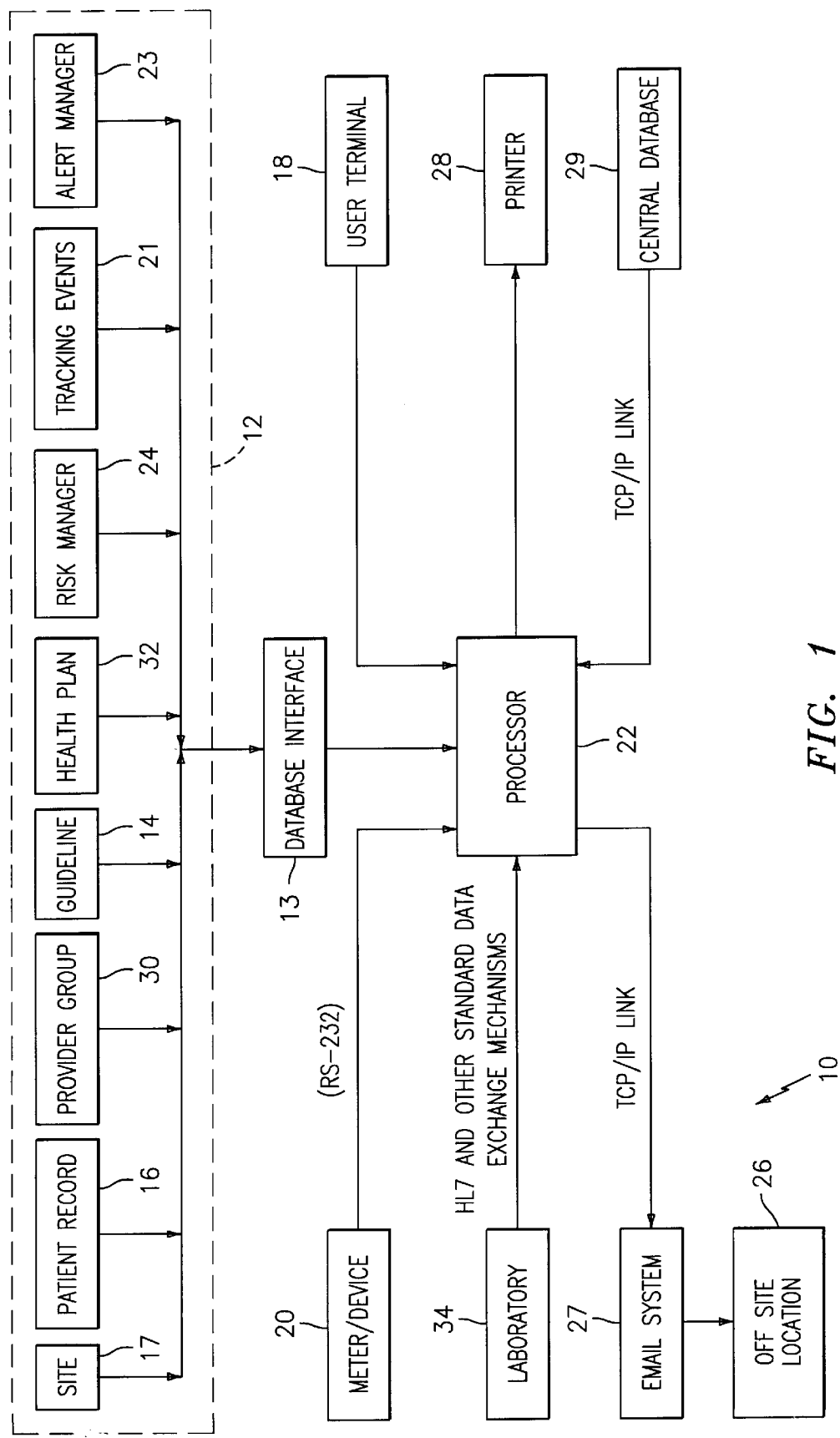
FIG. 1 is a block diagram of a chronic disease monitor of the type embodying the invention.

Referring to FIG. 1, a chronic disease monitor in accordance with a preferred embodiment is generally shown at 10. Chronic disease monitor 10 includes a central database 12 that electronically stores chronic disease information and enables a system user to access the stored information to monitor a chronic disease. Central database 12 includes computer memory in the form of RAM and ROM memory and is located in the computer hardware or deposited on a readable storage media. Guideline 14 comprises an algorithm representing known parameters of a chronic disease, including risk factors and complications associated with that disease, may be tailored by the medical provider to implement a facility wide treatment plan to a given patient population as well as on an individual patient basis. Patient record 16 information, such as demographic information 100 and insurance information 102, is inputted by user at user terminal 18, such as a computer terminal, a personal computer interfaced within a local area network, and the like. Site information 17 comprises data associated with the location of the installation (e.g. location, licensee, etc.). Patient information 16 is updated in a variety of ways. For example, a user may enter progress notes and/or test results at user terminal 18. Meter device 20, such as a blood glucose monitor, may provide test results in electronic data form. Processor 22 comprises a central processing unit, such as a microprocessor, which stores and accesses the information in central data base 12 (such as a patient record 16). Database interface 13 comprises a plurality of operating systems and programs allowing monitor 10 to store and retrieve data stored in database 12. Patient record 16 is applied to an algorithm within guideline 14. If a test result exceeds an expected threshold, an alert is generated and a notation is stored in risk manager 24. The alert may be communicated to an off site location 26, e.g. via e-mail 27, such as to an employer, health maintenance organization and the like, and/or a letter may be printed to the patient via printer 28. Additionally, if a patient fails to attend a scheduled service, an alert is similarly generated. Processor 22 may optionally be linked to a central database 29 (offsite) via a TCP/1P link as is known in the art.

Provider information 30 (e.g., a physician) and health plan information 32 are also stored in central data base 12, to enable communication with medical providers and third parties. While the chronic disease monitor of the present invention may be used for other chronic diseases, chronic disease monitor 10 is particularly relevant with respect to diabetes and therefore, hereinafter, the chronic disease monitor will be described with respect to the monitoring and control of diabetes.

Figure 2:
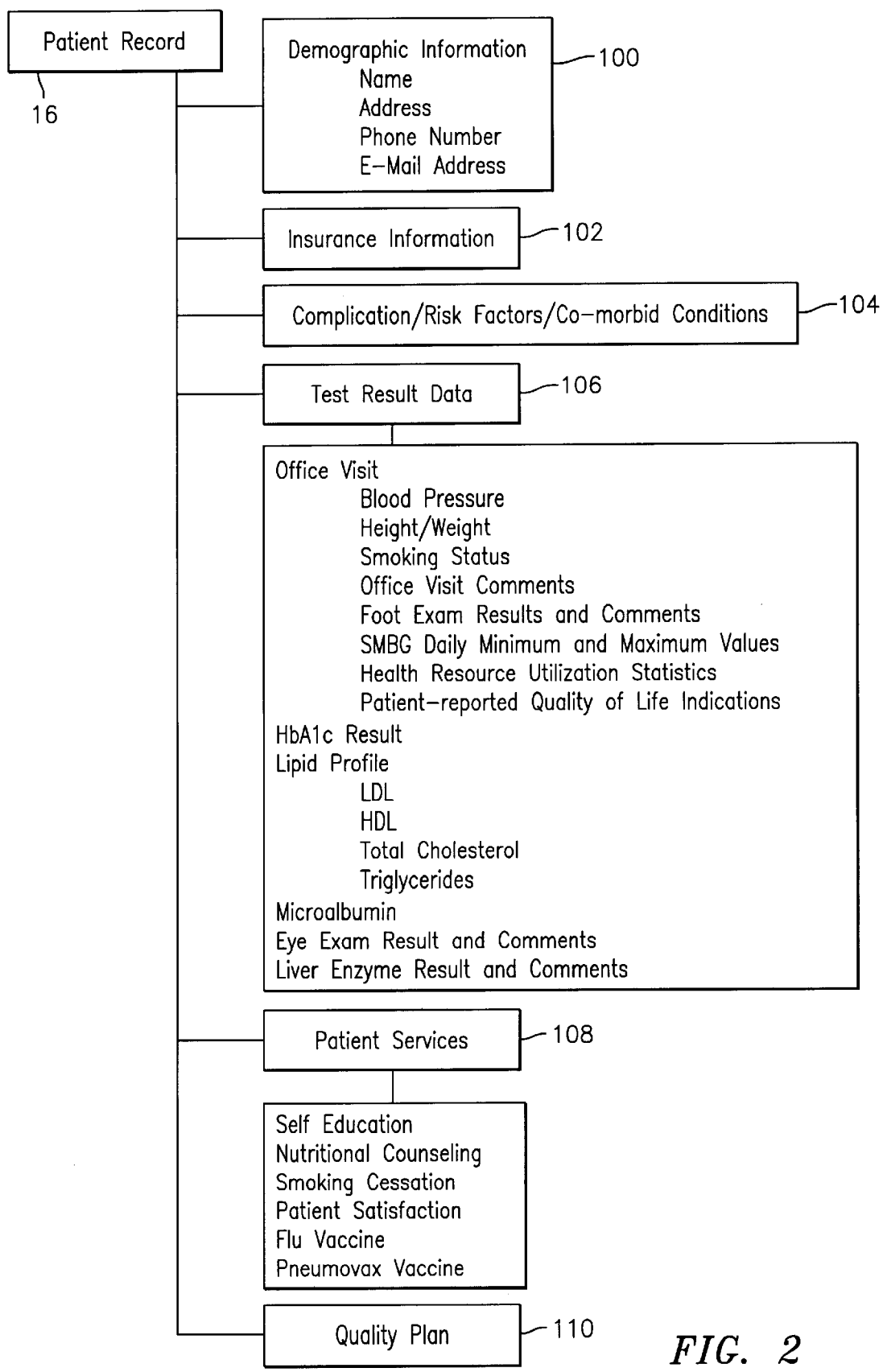
FIG. 2 is a block diagram illustrating a patient record.

Referring now to FIG. 2, patient record information 16 is generally shown in block diagram form and is described as follows. Monitor 10 incorporates a window format and is programed in Microsoft Visual Basic® to operate in an Windows® environment. It will be appreciated by those of ordinary skill in the art that other programing formats and/or languages may be employed. Patient record 16 is entered by a user at user terminal 18 and includes the patient's demographic information 100 e.g., salutation, name, gender, year of diagnosis, diabetes type (type 1, type 2, gestational), address, contact information (e-mail, work and home phone), initiation of care date, health plan, health plan id, provider, employer and language. Insurance information 102 is also recorded in patient record 16. An identifying number for the patient is stored in the data base. Additionally, complications, risk factors/co-morbid conditions 104 such as retinopathy, neuropathy, nephropathy, PVD, CAD and cerebral vascular disease are recorded.

Patient record 16 also include test data 106. Test data 106 comprises the office visit date, practitioner, office visit comments, such as progress notes and patient concerns, are recorded. Clinical information, i.e. weight, height, blood pressure, smoking status, blood glucose recordations (SMBG), lipids profile, liver enzyme, foot exams, neuropathy, skin condition, eye exam, are stored. It will be appreciated to those skilled in the art, the blood glucose information may be entered manually or electronically transferred from a blood glucose metering device 20, such as a Life Scan OneTouch. Data may also be transferred directly from a laboratory, such as via an RS-232 port or TCP/1P (FIG. 1) in HL7 (or other standard data format). Quality of life indicators, such as number of emergency room visits, days of hospitalization, days lost from work, and activities, provide important outcome information. By storing this information in patient record 16, reports may be generated comparing changes in these factors over a given period of time and/or for a selected treatment therapy. Combinations may be applied. Further, a patient's own self assessment is recorded as diabetes is such that success in treatment is heavily dependant on the patient's active participation.

Patient record 16 also includes a quality plan 110. Monitor 10 generates quality plan 110 from a selected guideline 14 and allows the user to customize the quality plan by selecting frequencies, thresholds and goals for a series of tests which are required to be performed on the patient, setting alert values if thresholds are exceeded or if tests are not undertaken. For example, tests for HbAlc, lipids (to measure cholesterol), blood protein (microalbumin), eye and foot examinations are recommended by the American Diabetes Association. As described in greater detail below, the frequencies for these examinations are defaulted to the recommended ADA values (but may be over-written by the user). Additional tests may be programmed, such as a stress test for cardiovascular disease. The frequency of office visits may be stored. Monitor 10 notifies providers, health care plans and patients via letters, e-mail, etc. Letters may be stored in the form of reminders, and/or report letters, indicating test results, a missed appointment, an alert and the like. Patient services 108 including self-education, nutrition counseling, smoking cessation, patient satisfaction, flu vaccine and pneumonia vaccine are also stored in patient record 16. Patient record 16 also includes a patient's medications, therapies and treatments (such as medication, dosage, frequency start date, a nutrition plan and exercise plan).

It will be appreciated by those of ordinary skill in the art that the window environment allows the user to access this information from window to window and that additional information may be optionally stored "behind" the window in layered fashion.

Figure 3:
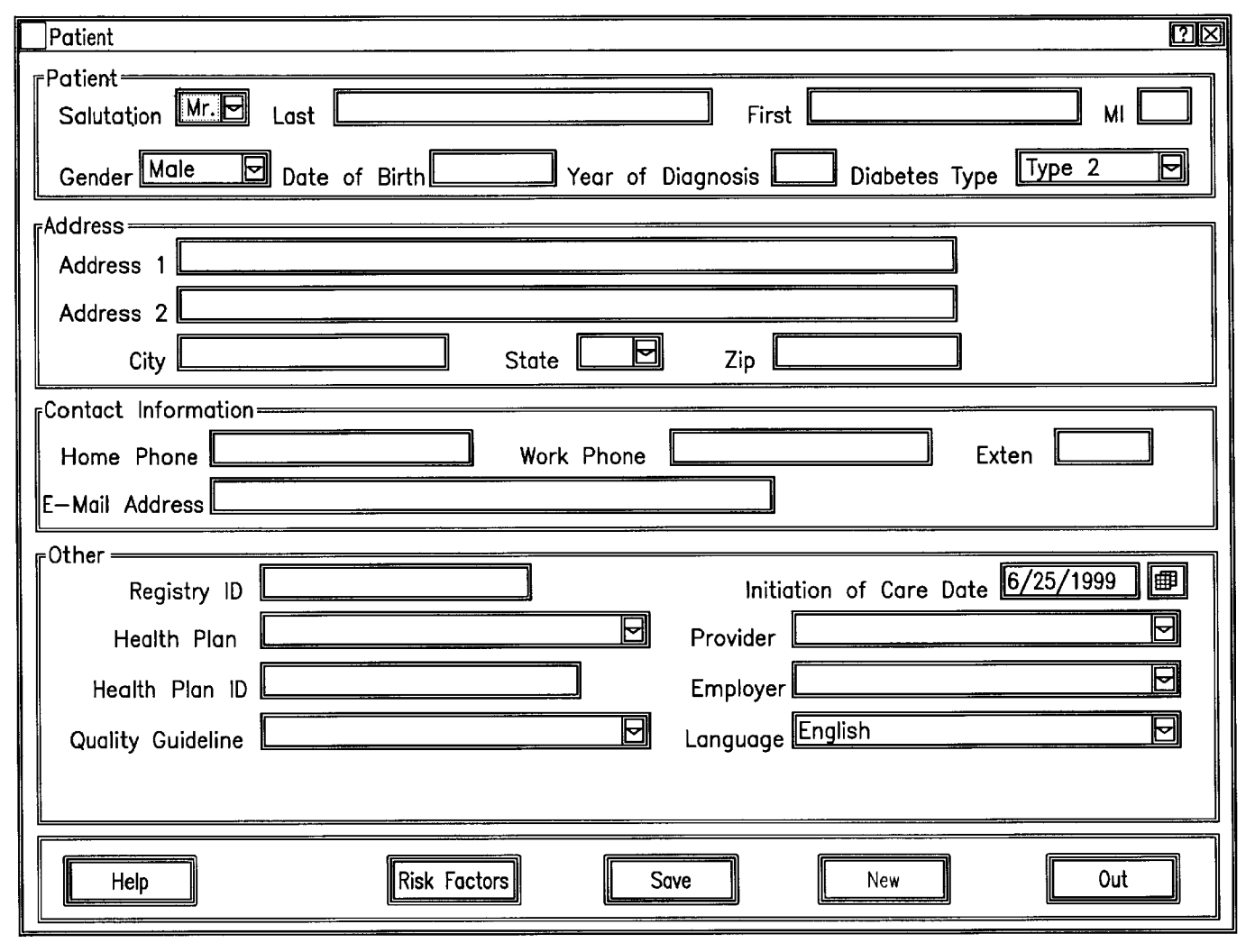

As shown in FIGS. 3 through 7, patient data 16 is presented to a user in a window format, though other known program formats may be used. FIG. 3 illustrates the patient setup, where the user may input the patient's demographic information 100, such as salutation, name, gender, date of birth, year of diagnosis, diabetes type, address, contact information, registry ID, health plan, quality guideline, provider, employer and language. FIG. 4 illustrates a second portion of the patient setup where the user may select complications, risk factors/co-morbid conditions 104 which the patient suffers, such as retinopathy, neuropathy, nephropathy, PVD, CAD and cerbro vascular diseases.

Figure 5:
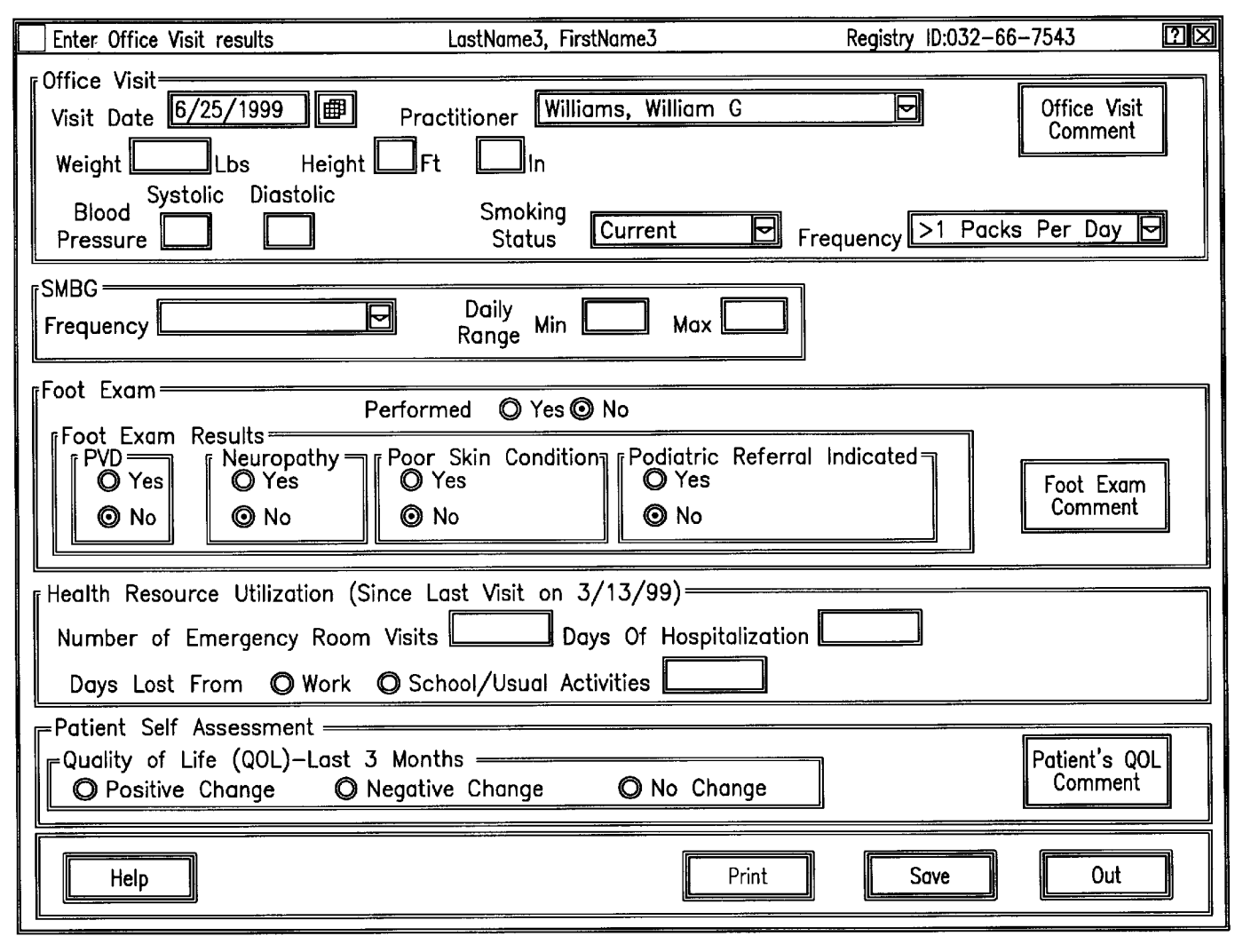
Figure 6:
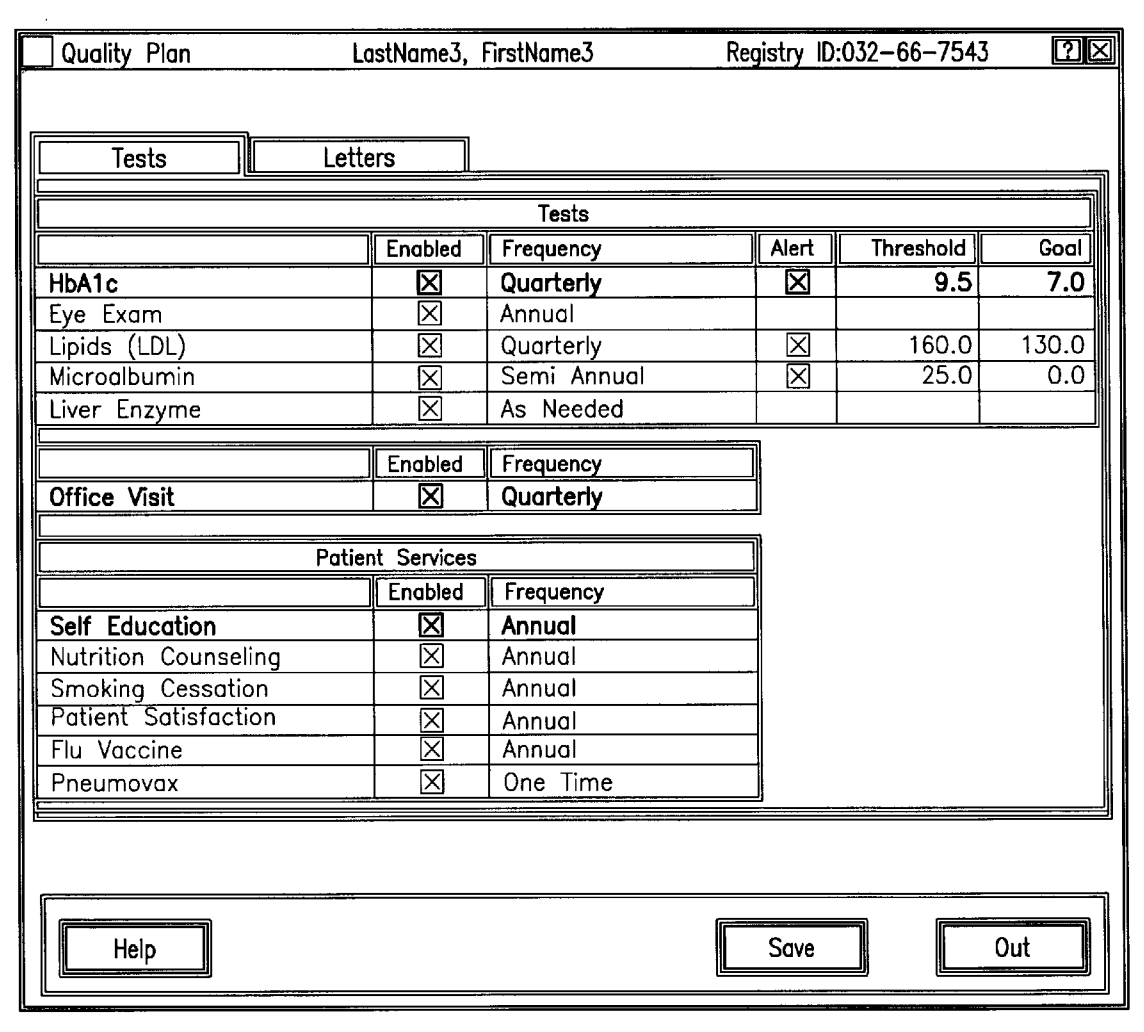

FIG. 5 illustrates a window which is prompted when office visit data is entered into patient record 16. The user may enter the office visit date, practitioner, weight, height, blood pressure, smoking status, blood glucose (SMBG) and daily range, foot exam (PVD, neuropathy, poor skin condition, podiatric referral), quality of life indicators (number of emergency room visits, days of hospitalization, days lost from work) and the patient self assessment. FIG. 6 illustrates a window which is prompted for the creation of a patient quality plan 110. The tests to be preformed on the patient are selected for enablement, frequency, alert (where a value is exceeded), threshold and goal. As described in greater detail below, the values for the threshold default to the guideline value located in guideline 14 generated for the patient population in risk manager 24. The user may enter a different value for a given threshold and override the guideline default. The user is prohibited from entering a threshold value which would be impossible (outside of permissible test ranges, for example) and which is greater than the patient population threshold. FIG. 7 illustrates a current therapy plan data record in patient record 16 as presented to the user in a window format. The user may input comments. The information is classified by medication type, medication, dosage, frequency and start date. The nutrition plan summary and/or exercise plan summary may also be entered.

Figure 8:
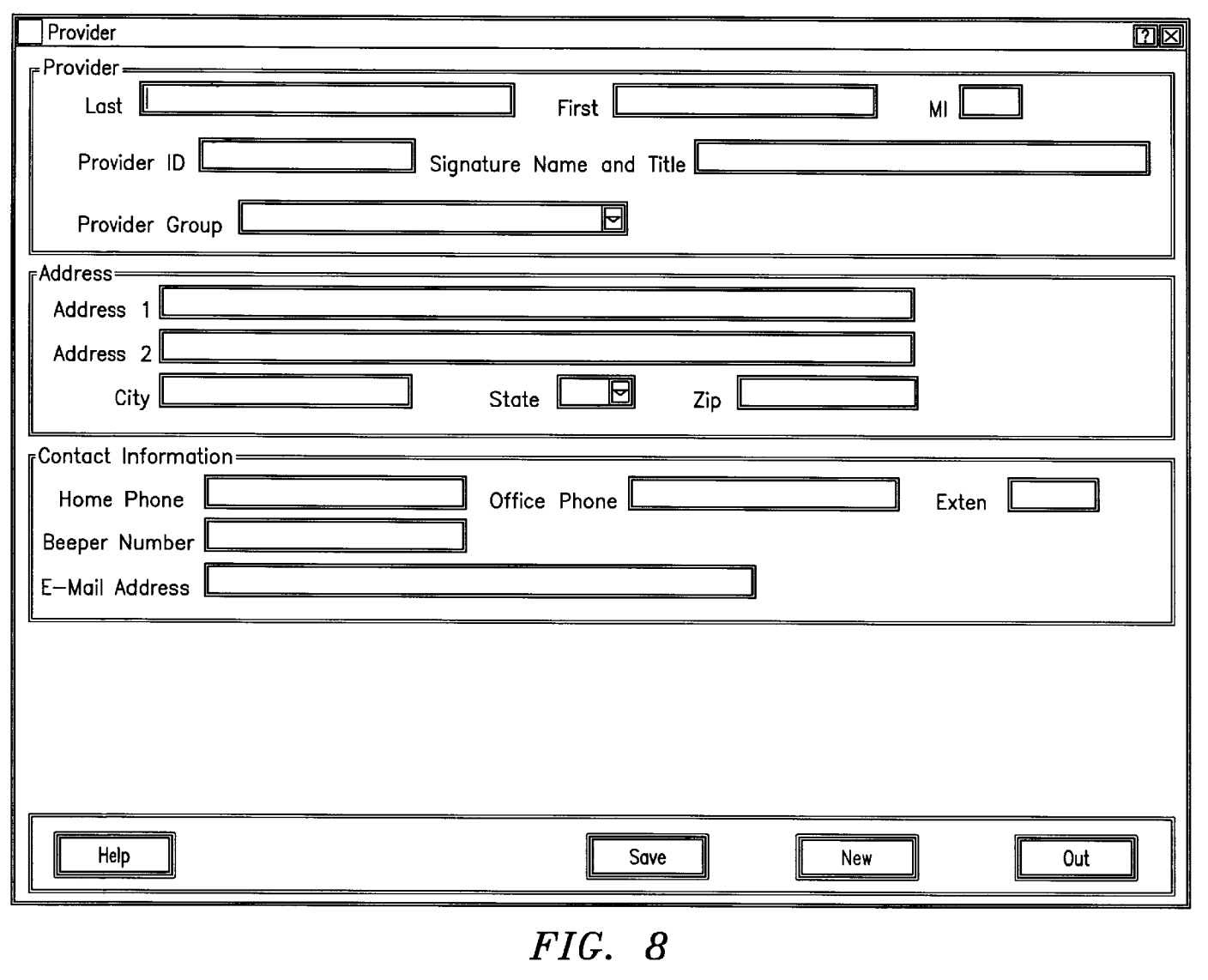
Figure 9:
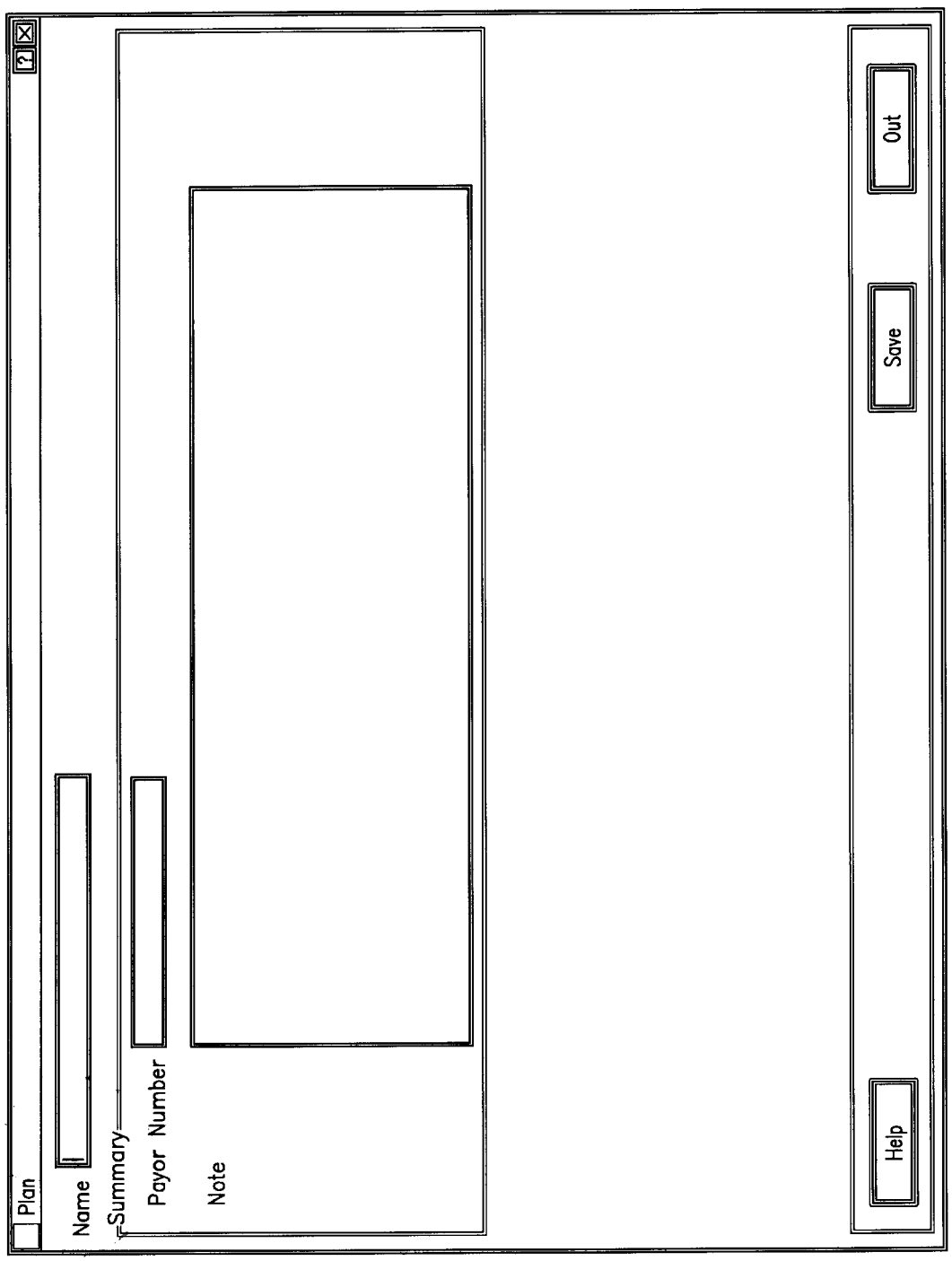
FIG. 9 is a graphical window displayed to a user entering a health plan record.
Figure 10:
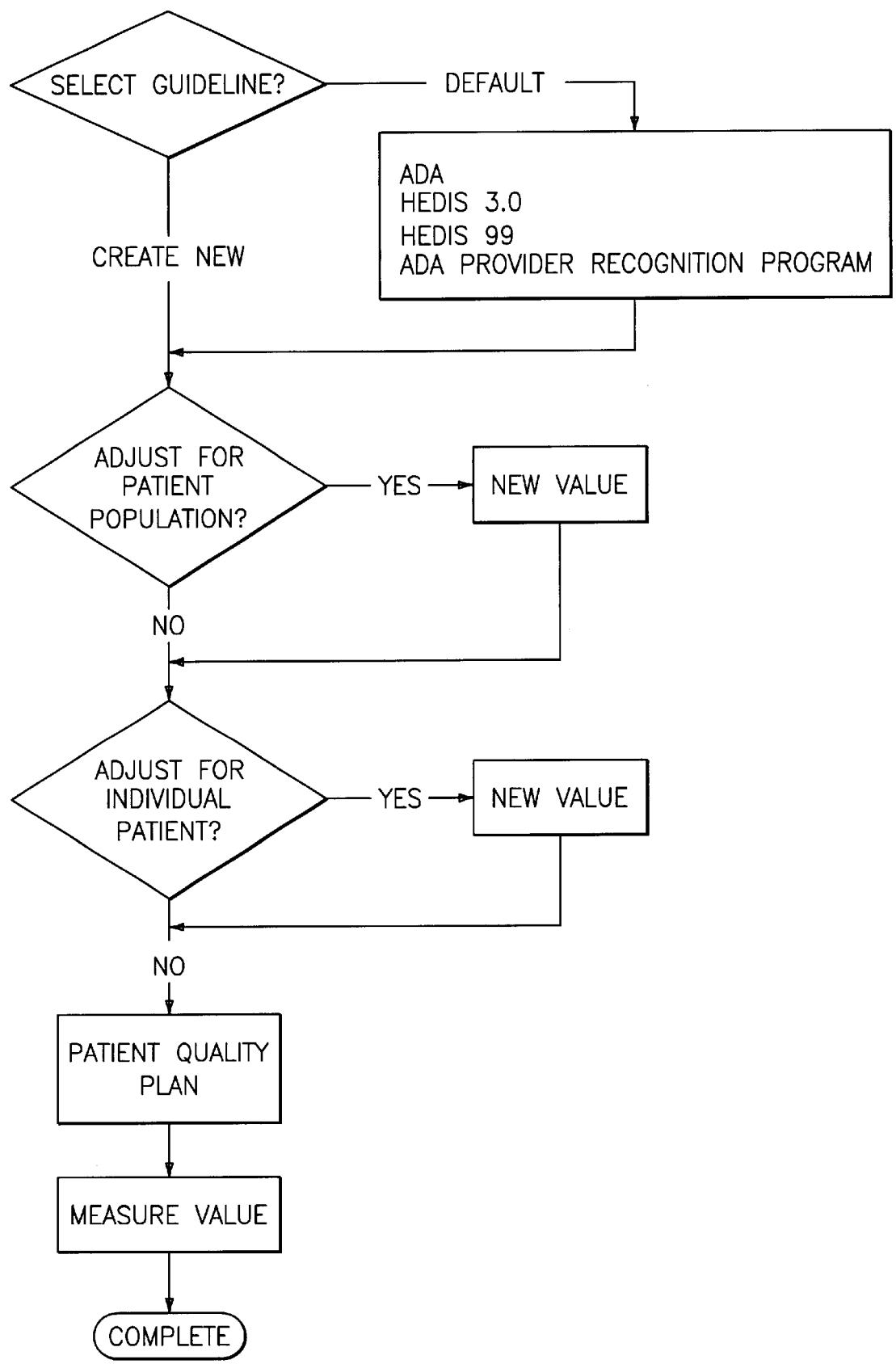
FIG. 10 is an algorithm for creating the guideline applied to the patient data record.

Referring now to FIG. 8, provider information, such as for a physician, including the name, address, identification number, contact information, beeper number and the like stored in database 12 as provider record 30 is generally illustrated. The user is prompted with a window which allows the user to enter the information. FIG. 9 illustrates a window for receiving health plan records 32. The user may input comments concerning specific policies which are recorded in health plan record 32.

Referring again to FIG. 1, guideline 14 comprises an algorithm which represents the diabetic treatment model recommended by the ADA. Guideline 14 represents the recommended tests (and frequencies), alert thresholds and goals for the care of the diabetic patient. A user may use an ADA default, may program a different set of thresholds for a patient population, and may adjust the parameters for each patient to establish a quality plan. The ADA publishes standards entitled HEDIS (Health Plan Employer Data and Information Set) 3.0, HEDIS 99 and the ADA Provider Recognition Program. These standards contain recommended (and accepted) treatment schedules for the diabetic patient. For example, HEDIS 99 requires quarterly HbAlc testing, annual eye exams, annual lipid profile and annual microalbumin exams. Typically, the alert threshold for the HbAlc test is 9.5%, with a goal of at least 7.0%. Similarly, the annual lipid profile, typically has a goal of 130 Mg/dl and an alert threshold of 160 Mg/dl. Microalbumin exams have a goal of 9, with an alert threshold of 25 Mg/L. Thus, these parameters are incorporated into a rule structure for the monitoring of the diabetic patient. As described in greater detail below, the user may select a rule for the treatment of the patient population. For example, the data may sorted for all patients having hypertension and having a blood glucose test level exceeding 9% HbAlc. For each patient data entry, a comparison is made between a guideline value (measure value) in guideline 14 and the test data from patient record 16 to determine if the rule is satisfied and/or whether a threshold level has been exceeded.

Turning now to FIGS. 10, 11A, 11B and 11C, the logic sequence of guideline 14 and risk manager 24 will be explained in greater detail. The ADA has published recommended guidelines for the treatment of diabetes. These guidelines are based on years of study of the disease and comprise the recommended treatment for individuals suffering from the disease. For example, the HEDIS 99 guideline sets as an alarm threshold for microalbumins greater than 25 Mg/L, which indicates a patient who requires immediate medical assistance. This value is stored in guideline record 14 as a default value. The user may select a default guideline, such as the ADA HEDIS 3.0, HEDIS 99 and/or ADA Provider Recognition Program. Alternatively, the user may create a guideline for any and/or all of the measures (HbAlc, eye exam, lipid (LDL), microalbumin, liver enzyme, self-education, nutrition counseling, smoking cessation, patient satisfaction, flue vaccine, and pneumonia vaccine. The user may also modify the ADA rule and enter a new threshold limit in place of the ADA guideline default in guideline 14 for a given patient population, e.g. for all patients covered under a certain plan, associated with a certain physician, and the like. Additional rules, representing threshold values, may be selected. For example, patients with HbAlc value of greater than 9.5%, or patients who have not been tested, who also have an associated risk factor for hypertension, may be selected by the user to create a rule within guideline 14 to be applied to the database 12. A HbAlc reading of 9.5% or a patient having the risk factor of hypertension would mean that the patient is at high risk and needs immediate medical treatment. Incorporated in the guideline 14 are known parameters for the disease of diabetes so that a user may not input a value which would be outside of possible testing values. If the ADA guideline value is not adjusted, then it will be the default value for the individual patient for the generation of a patient quality plan. Alternatively, the patient population default value may be adjusted for an individual patient for incorporation into the patient's quality plan. The value assigned in the patient quality plan is the measure value against which test results and clinical events are compared.

A test result may be communicated from Laboratory 34 via an RS-232 port directly to the processor 22, may be blood glucose data generated from a hand held blood glucose meter device 20, and/or may be manually inputted by a user at user terminal 18 and recorded in record 16. A clinical finding or notation, such as a missed service, a new complication, a measurement and the like may also be entered and stored to be applied to the guideline 14. The value is compared against the measure value derived from the patient's quality plan 110. If the test result/clinical event exceeds the expected measure value (or a scheduled service or event is missed or omitted), a series of program functions are performed. The functions resulting from the threshold value being exceeded and/or from the application of a rule, may be generally described as an action sequence. Whether the action sequence is activated or no action is taken, the patient's record 16 is updated to reflect the test result/clinical event. If the alert function has been selected in the patient record 16, an alert for the patient to alert the system manager and/or medical provider/physician of the event is registered. Also, the patient's name is added to the risk manager 24, a letter is generated to send to the patient (and/or another physician or caretaker), the information is communicated off site 26, such as to a health maintenance organization, provider, and the like. Also, the patient's quality plan 110 in patient record 16 may be updated to reflect the necessity for additional tests and/or a different frequency or parameter for the tests as a result of the exceeded threshold. The clinical schedule is also updated to reflect the patient's need for additional services. Alternatively, a report letter, with encouragement concerning the test result, and/or explaining the test result, may be sent to the patient.

Figure 11A:
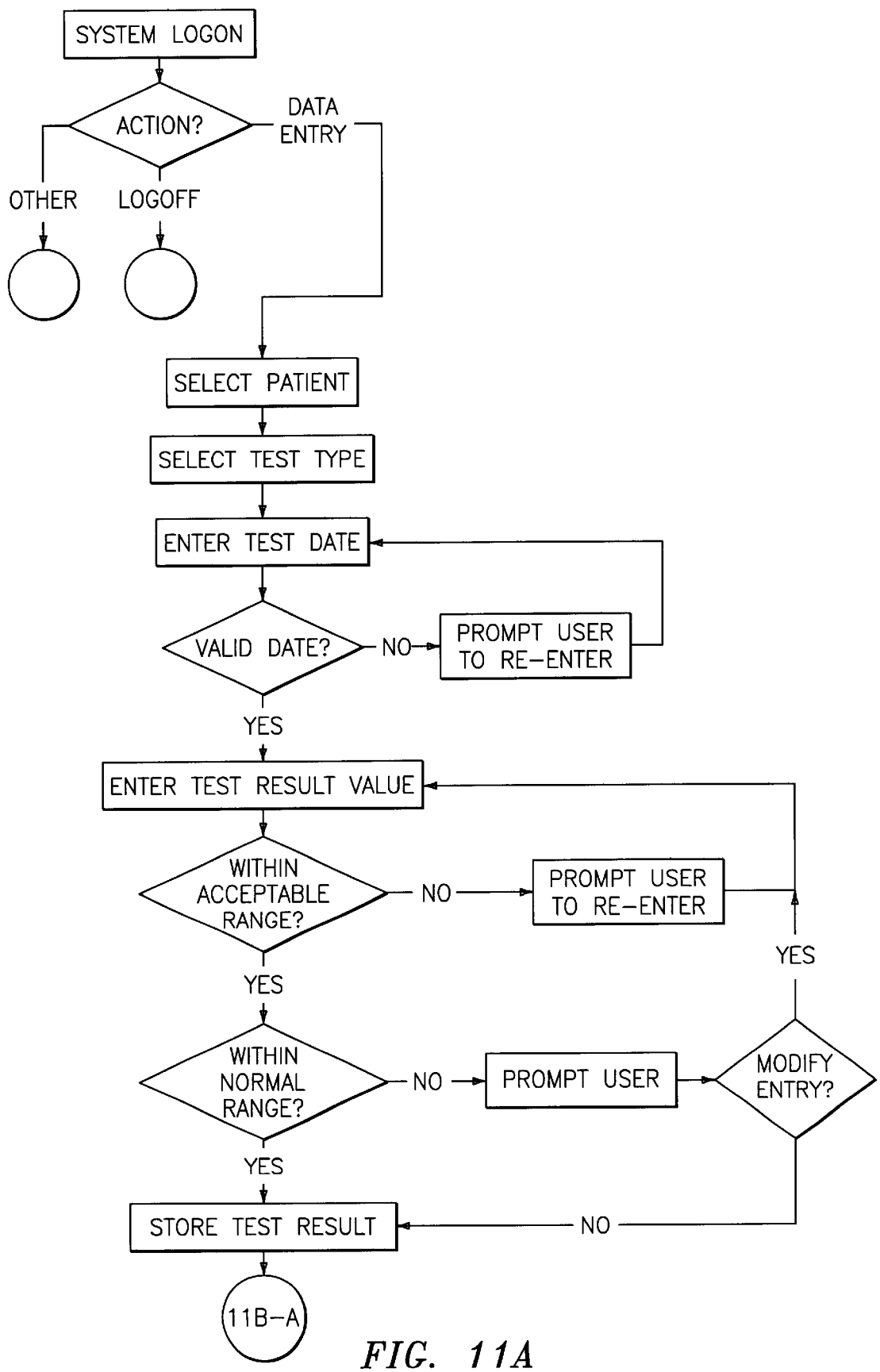
FIGS. 11A–11C is an algorithm illustrating the application of the guideline to the patient record.
Figure 11B:
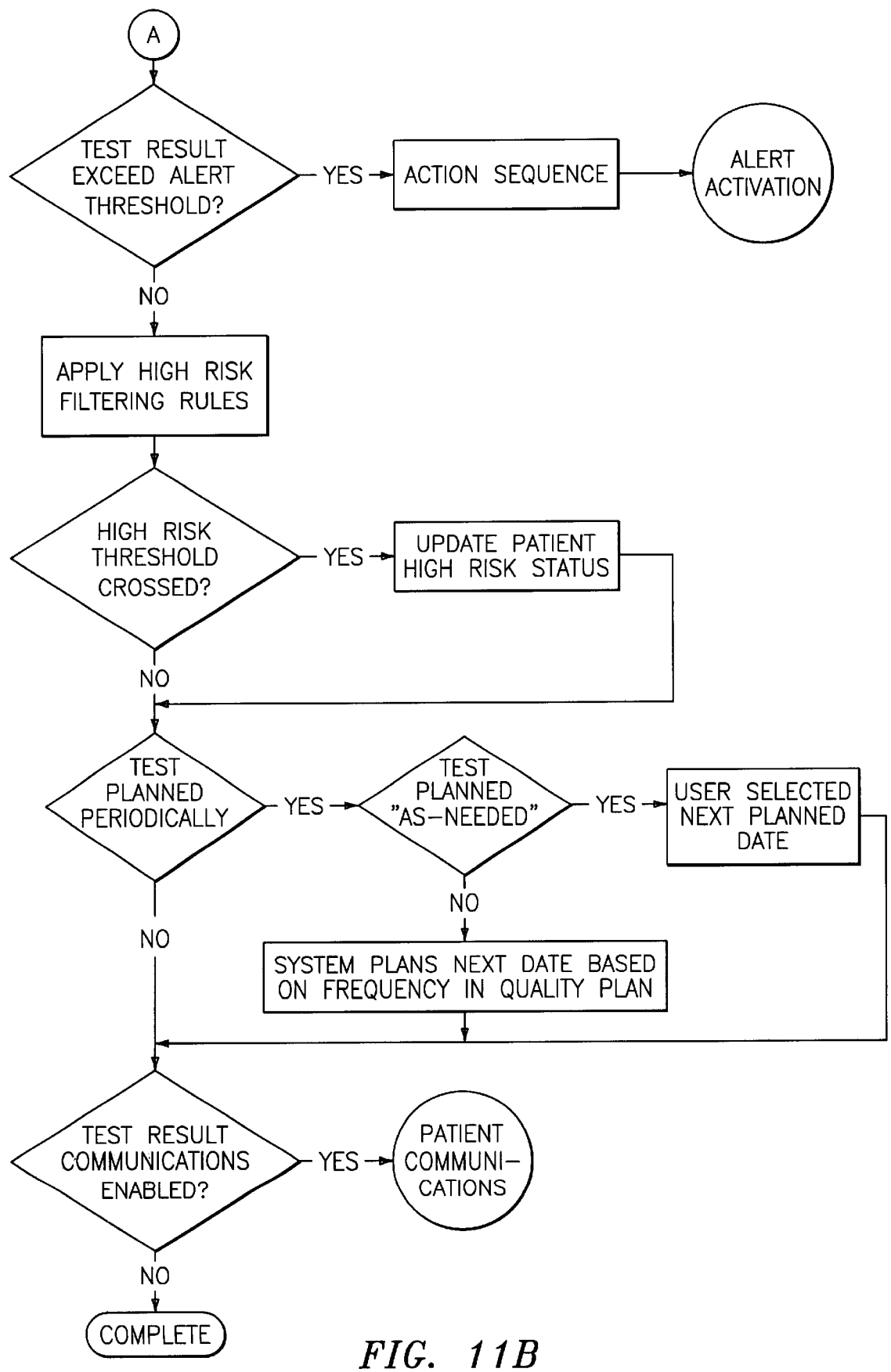
Figure 11C:
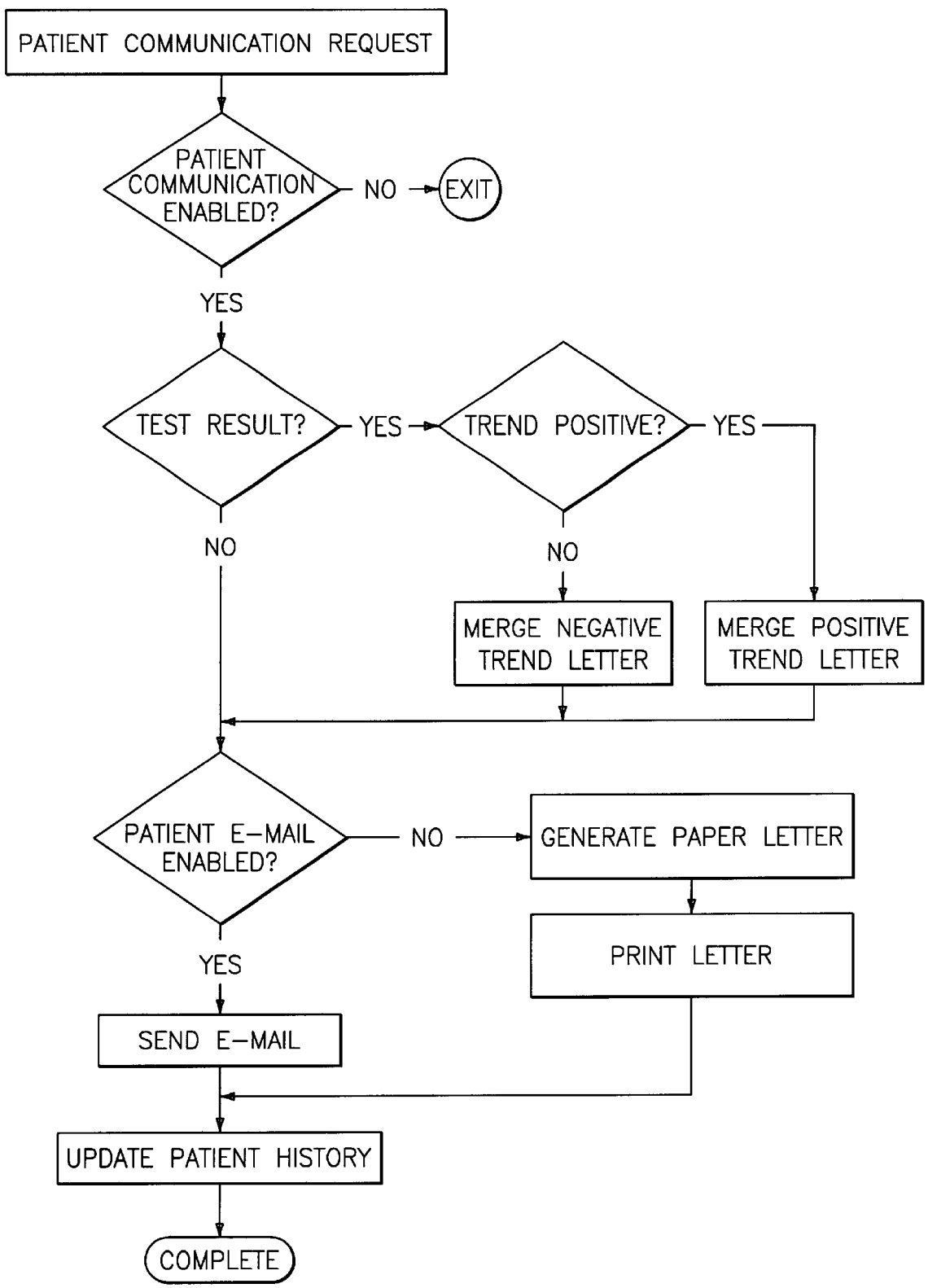

Referring now to FIGS. 11A through 11C, the user logs onto the system from user terminal 18 and selects an action. The user may access the data records stored on central data base 12 and/or may chose to enter data (a patient record 16 is then selected). The test type is selected. The test date is then entered. If the date is invalid, i.e. a date in the future or an impossible date, e.g. 1867, Monitor 10 will prompt the user to reenter. The user then enters the test value. If the test value is outside an acceptable range (known physical parameters) the user is prompted to again reenter. Similarly, if the test value exceeds normal values, but possible values, the user is prompted to confirm the value. If the data is entered via a meter/device 20 or other electronic device, an alert report is generated (if the data exceeds known parameters). After the data is stored it is compared to the guideline value (measure value). As set forth above, the guideline value may be a threshold for a test result and/or may comprise a rule combining a test threshold and a complication. If the threshold is exceeded and/or if the rule is satisfied, the action sequence is undertaken (i.e. alert, letter, offsite, update quality plan, update clinical schedule, add to risk manager, etc.). The data is then measured against the high risk monitor. If the high risk threshold is crossed, the high risk status is updated. Next, the planned events data within the patient record 16 is updated based on the criteria for the quality plan. For example, if the test is scheduled "as needed", the user is prompted to select a date. If there is another selected frequency for the test, such as quarterly, Monitor 10 will automatically schedule the test. If the test result communications is enable, the patient then receives notification of the test result and/or new test date. If it is a test result communication, the trend is determined (positive/ negative). Next, the patient e-mail enablement is determined. If yes, the communication is e-mailed. If no, a letter is generated. Patient record 16 is then updated.

Figure 12:
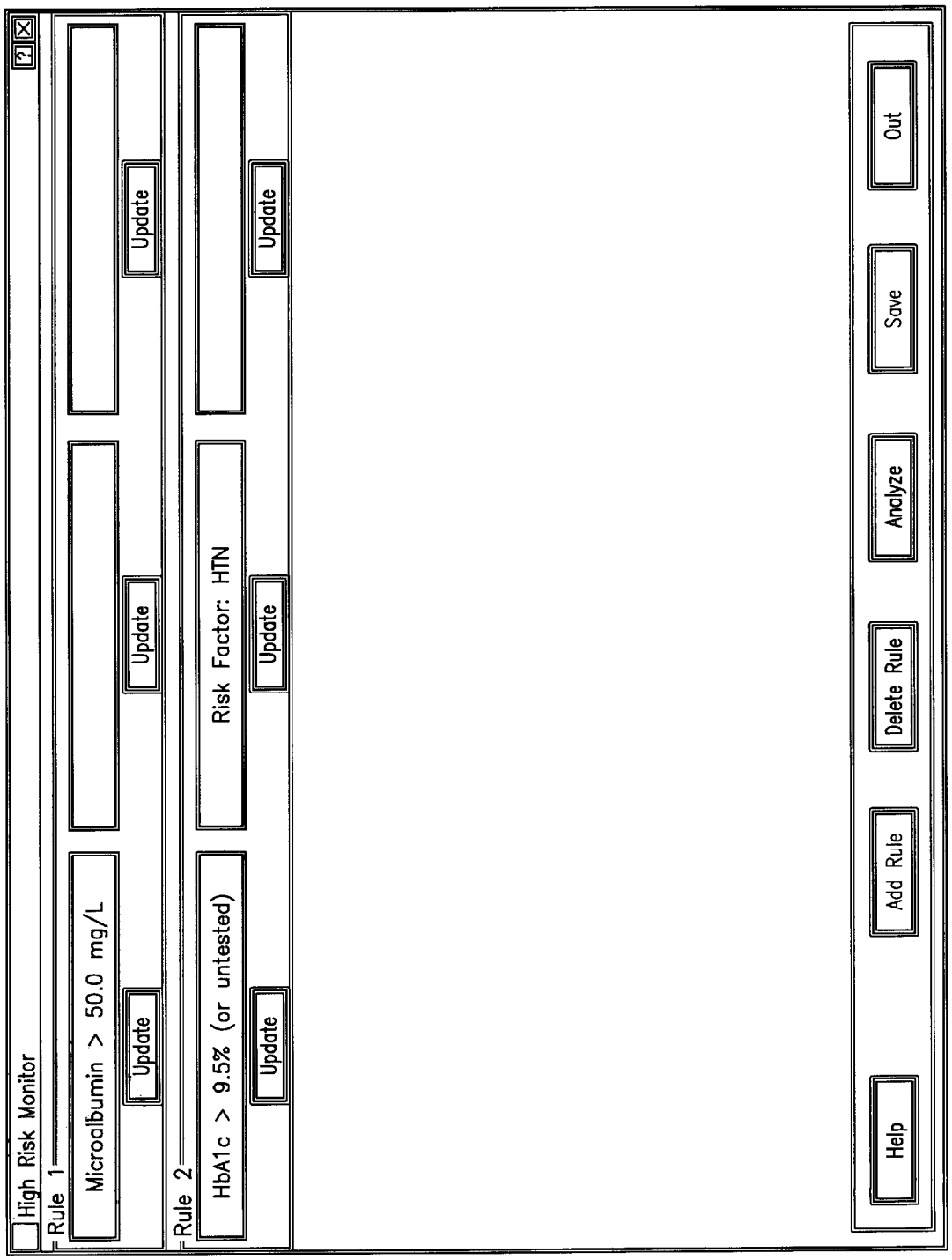
FIG. 12 is a graphical window displayed to a user entering a risk manager record.

Thus, for example, a user selects the high risk monitor in the menu driven format at user terminal 18 and adopts a rule for HbA1c≧9.5% (or untested) for patients with the risk factor of hypertension. As shown in FIG. 12, which illustrates the data entry prompt for the user when accessing the risk manager 24, the user may create a series of rules to be applied to a patient population by entering a threshold, risk factor and the like. For example, as illustrated in FIG. 12, if Rule 1 set the threshold for microalbumin levels >50.0 mg/L and Rule 2 set HbA1c>9.5% (or untested) for patients with hypertension, if either condition is met, the patient's name will be added to the high risk patient list (and the action sequence will be applied). Thus, if the microalbumin level exceeds 50 mg/L (Rule 1) or if the HbA1c test value exceeds 9.5% and the patient has the complication of hypertension (Rule 2), or if the patient has not been tested (Rule 2), the patient's name is added to risk manager 24. The action sequence is also initialized (i.e., alert, quality plan is updated to reflect the need for additional services, such as greater frequency in testing blood glucose, information is sent off site 26 to a pay provider, employer, health maintenance organization and the like, a letter is generated to the patient, and the appropriate physicians receive an alert concerning the test result/clinical event). If a test result/clinical event was less than the measure value of less than 50.0 mg/L microalbumin (Rule 1) and 9.5% for HbA1c (Rule 1), patient record 16 is updated and the action sequence is not executed.

Figure 13:
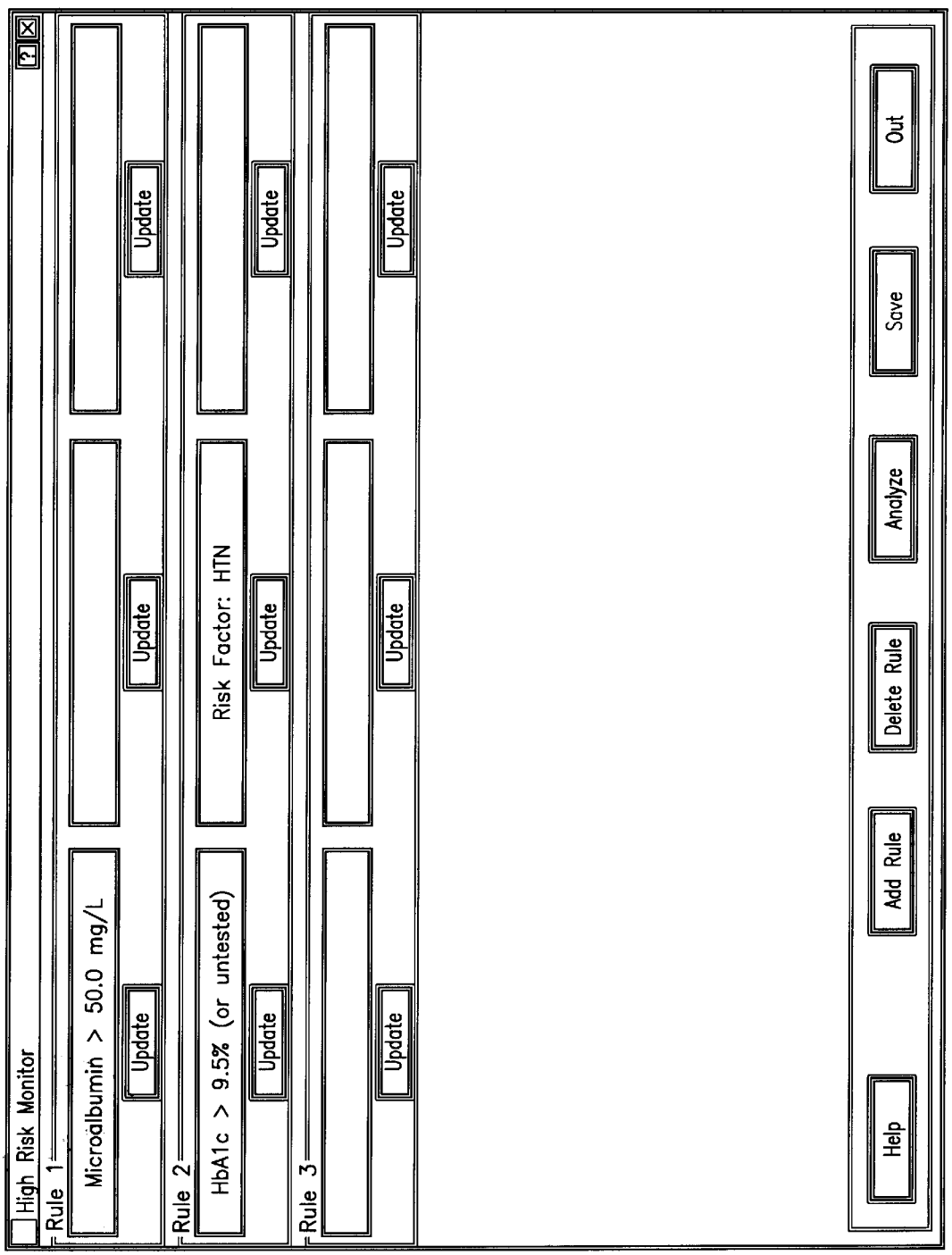
FIG. 13 is another graphical window displayed to a user entering a risk manager record.
Figure 14:
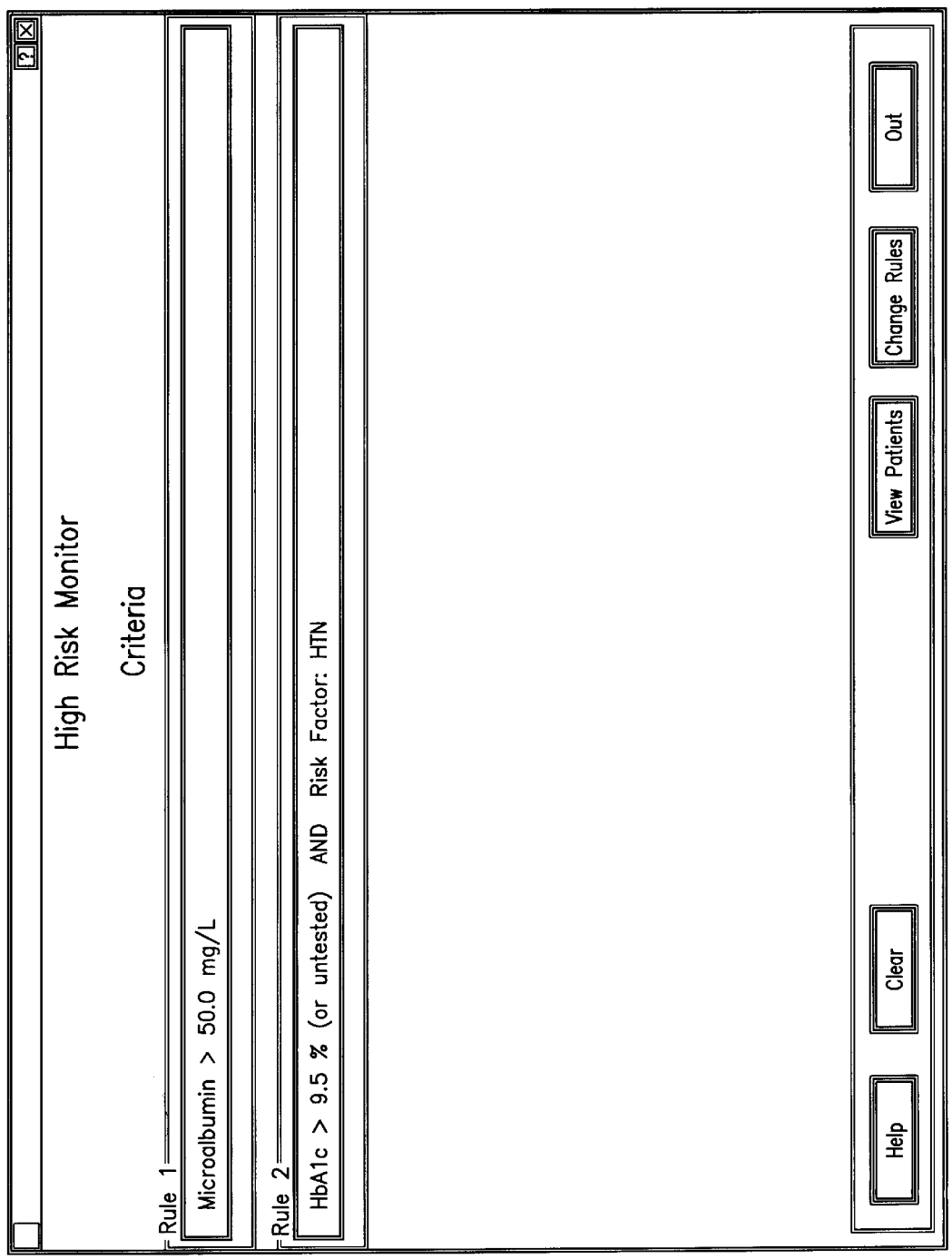
FIG. 14 is another graphical window displayed to a user entering a risk manager record.

Referring to FIGS. 13 and 14, risk manager 24 data is inputted by a user at user terminal 18. A window may be employed to prompt the user with respect to the data to be entered. The user may add a rule, deleted a rule, analyze the patient records 16 by rule, and change a rule.

Figure 16:
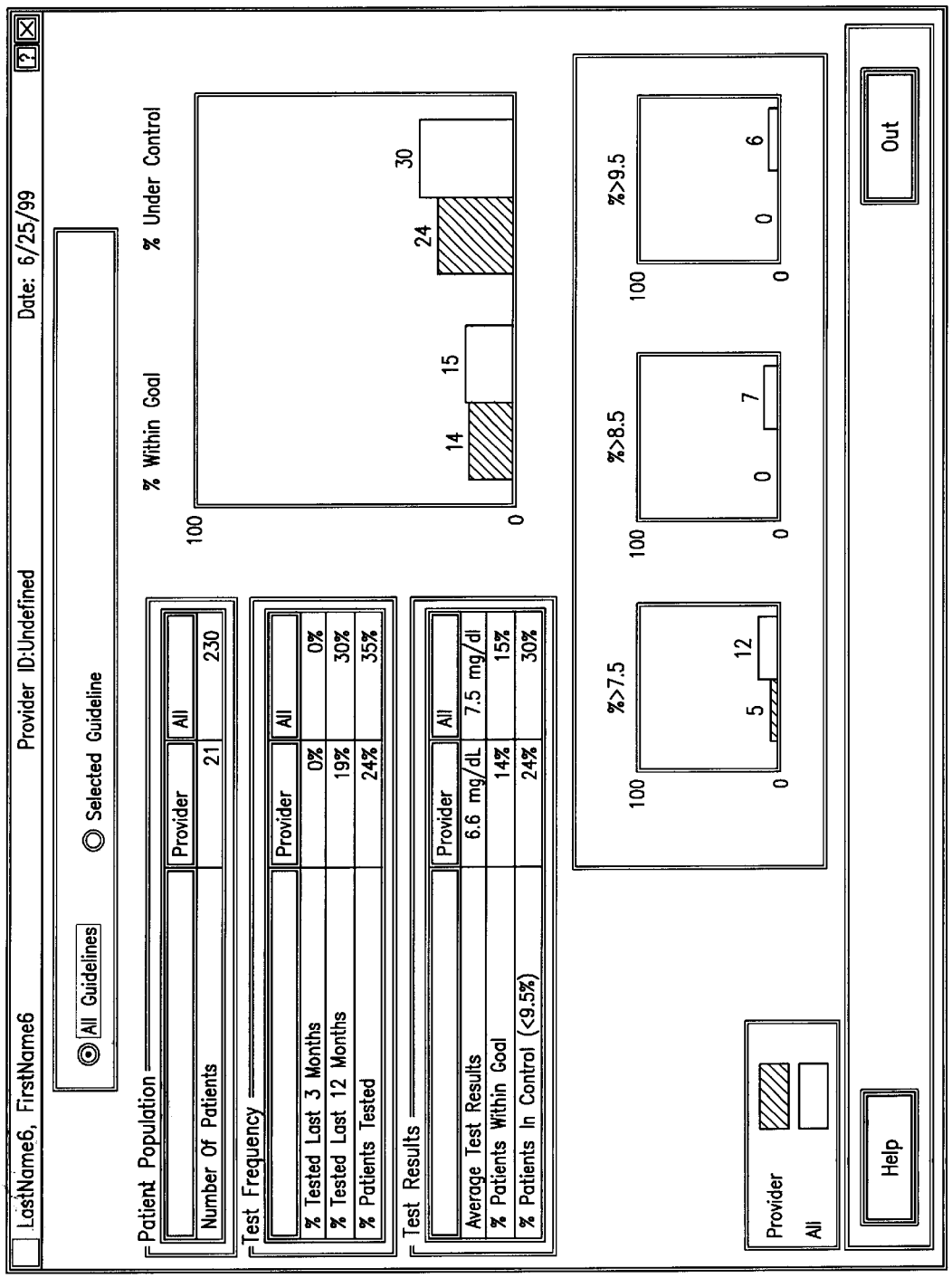
FIG. 16 is a graphical window displayed to a user entering a provider record.
Figure 18:
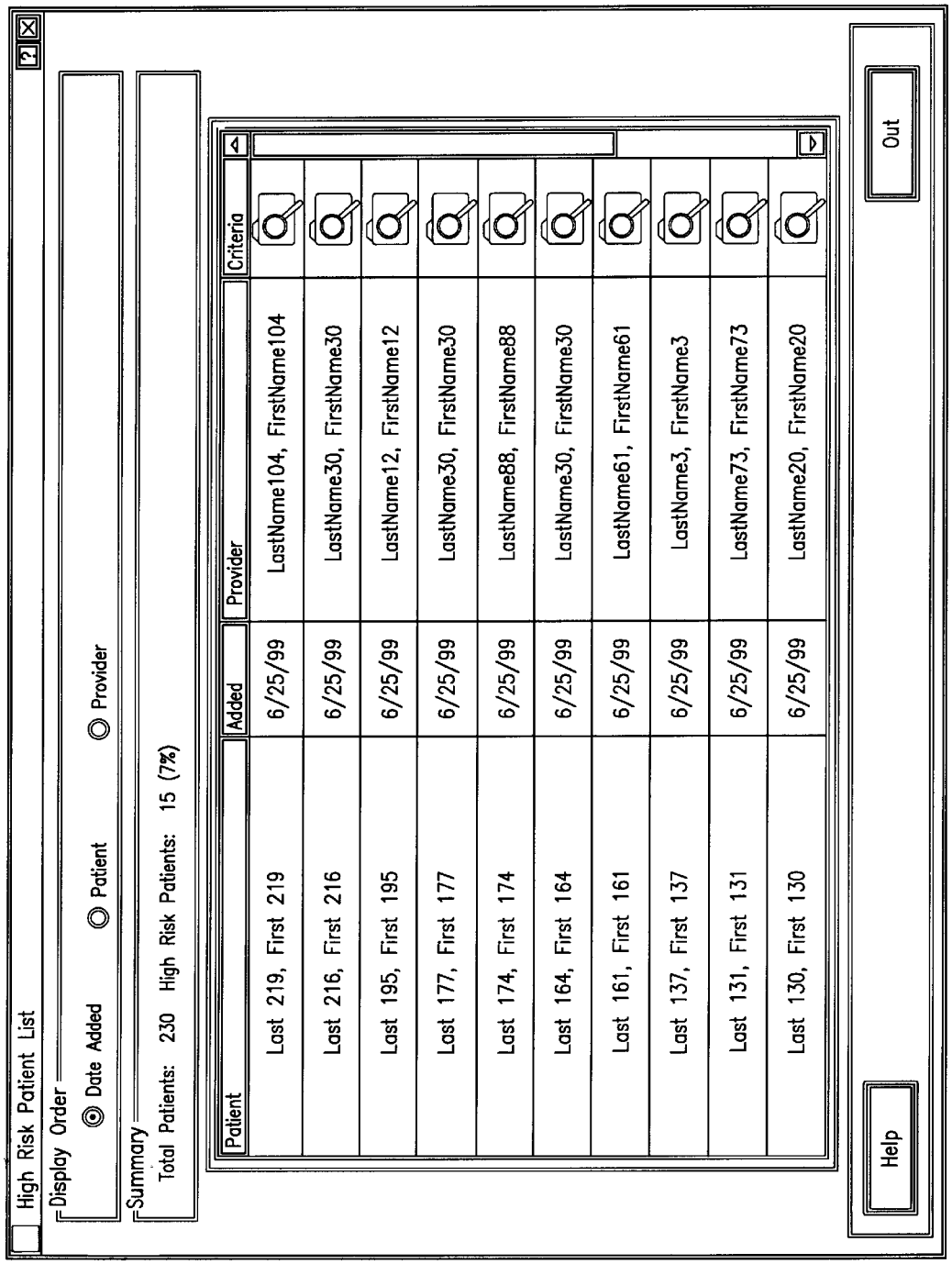
FIG. 18 is a graphical window displayed to a user entering a high risk patient report.

Referring to FIG. 15, an example of the type of report which may be generated as a result of the chronic disease monitor 10 is illustrated. It will be appreciated to those of ordinary skill in the art, that by applying the guideline and logic sequence described herein, that various reports may be generated to assist the physician, patient, and/or pay provider to monitoring the chronic disease. The user, via user terminal 18, selects the menu setting forth the provider record 30, which associates information with respect to a medical provider such as a physician. For the physician, the alerts are categorized by patient, date, test type, detail (goal, threshold, result). Reminders are also listed for the respective physician, indicating the date created, schedule, patient name, author and the subject. As illustrated in FIG. 16, the patient population may be viewed globally, settling forth the number of patients seen by the provider, the test frequency, test results, with graphical illustrations. Quality reports for patients, setting forth the patient population, including the category of diabetes, the number of patients and percentage of the patient population, the tests undertaken on the patient population, and the average result of those tests, are illustrated in FIG. 17. As shown in FIG. 18, a high risk patient list can be generated for distribution to providers, payers, etc. The background criteria is stored behind each high risk patient in window format. As illustrated in FIG. 19, a quality report by provider, setting forth the category, patients, percentage of patients by diabetes type, test (eye exam, foot exam, lipids, etc.) may be accessed.

As shown in FIG. 20, additional information, such as warning signs concerning symptoms and signs of foot disease may be stored (and optionally communicated to the patient).

As illustrated in FIG. 21, a report representing the patient's history using chronic disease manager 10 is shown. The information is categorized by date, event and detail. If an alarm has been generated, it is also illustrated. For example, if the patient goal for HbA1c, was 7%, and the test result value was 20%, applying the logic sequence as herein described using the guideline algorithm results in the action sequence causing the generation of the alert and the placement of the patient's name in the risk manager. The user may elect to see all entries. Alternatively, the user may select test results for a given patient by category, i.e. HbAlc, eye exam, lipids, microalbumin, may view quality guideline, quality plan, therapies, office visits, notes, reminders, patient communications, and meter selection by entering a check, such as with a mouse.

The user may also elect to change the rule and/or threshold in the risk manager. If so, the user will receive a warning, advising the user that the high risk patient list will be changed and the previous high risk patient list will be deleted. The user will receive a prompt, asking if the user wishes to continue. The user may elect not to continue and may then select another option in the risk manager or exit to select another function. If the user changes the threshold value (and/or rule) such as for lipids, HbAlc, etc., the new threshold, rule and/or Boulian combination thereof, will then be compared to the patient data. If the value is exceeded for the patient (or if the rule is satisfied), the action sequence is undertaken, and the alert, letter, offsite, clinical schedule, and risk manager are updated.

Figure 22:
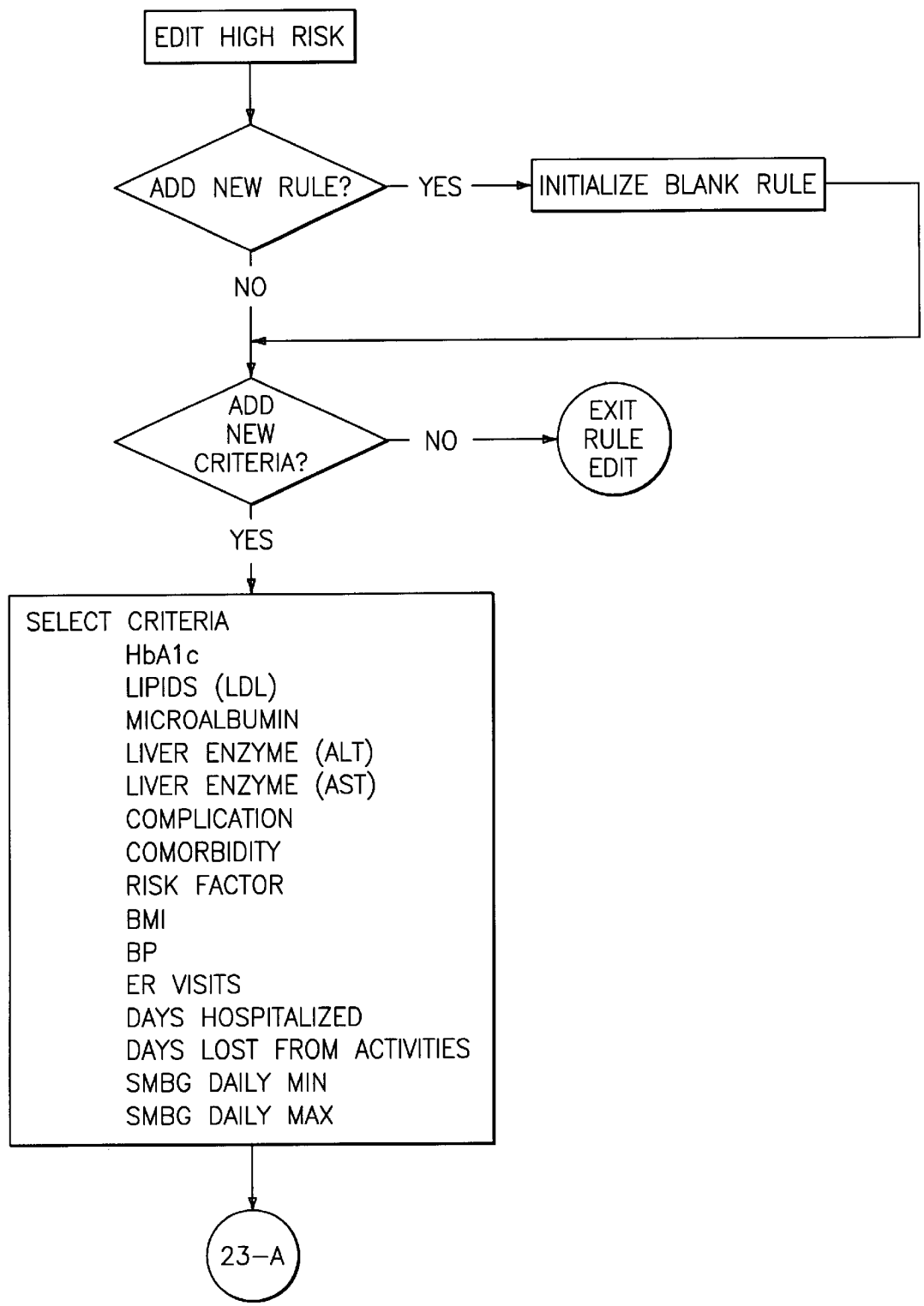
FIG. 22 is a block diagram representing the logic sequence for generating a high risk rule.
Figure 23:
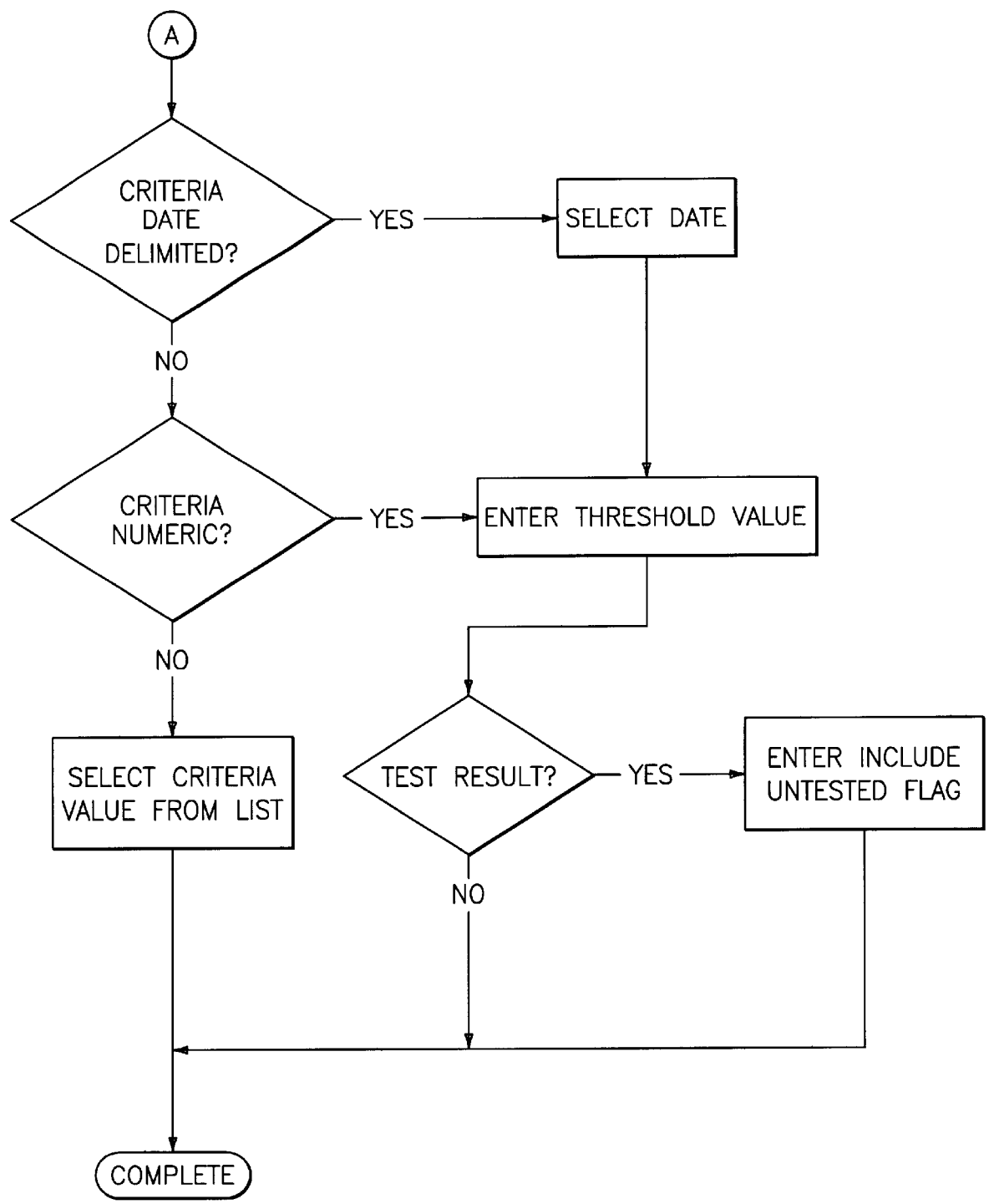
FIG. 23 is a continuation of the sequence of FIG. 22.
Figure 24:
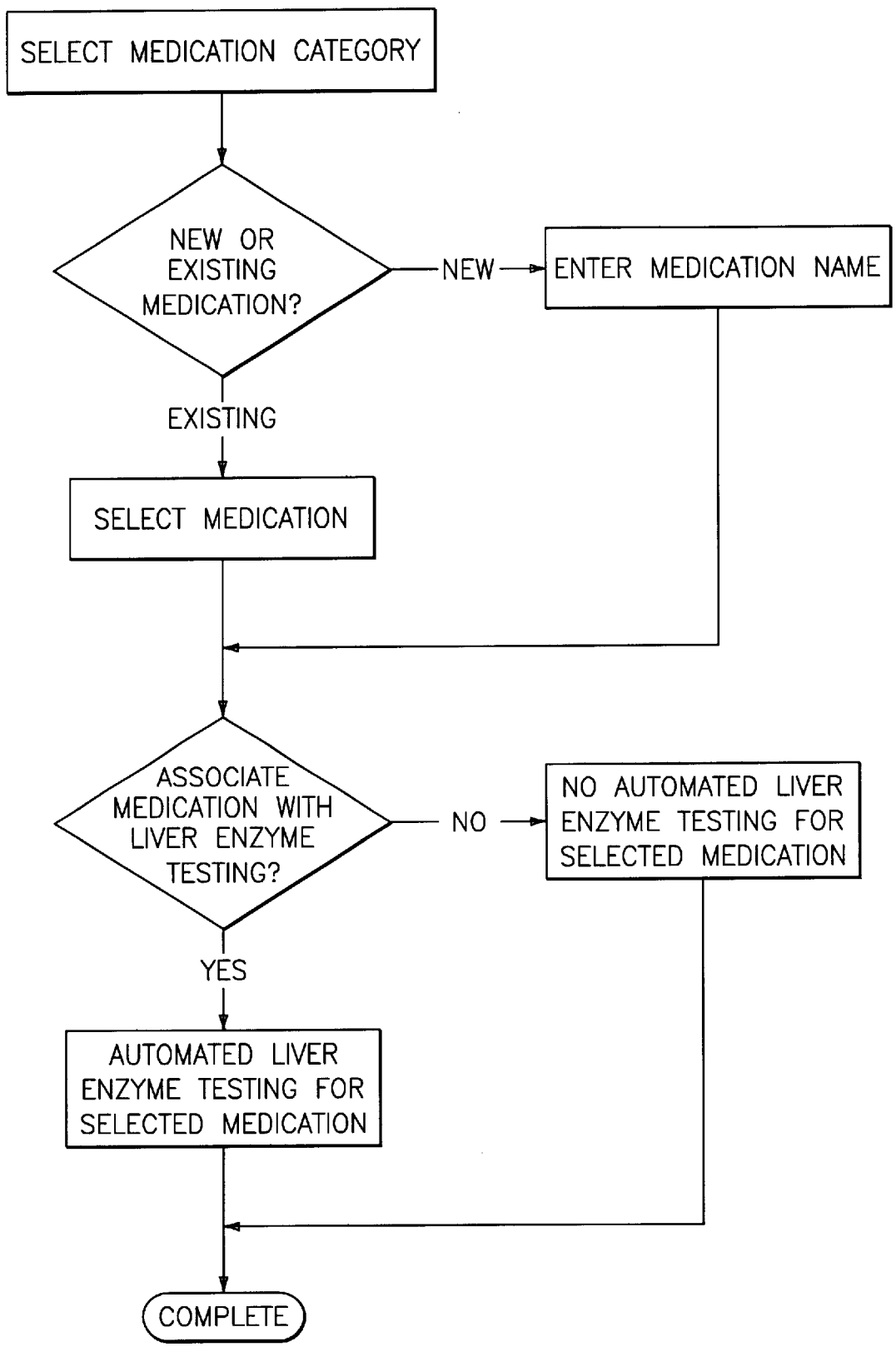
FIG. 24 is a block diagram representing the logic sequence for a generation liver enzyme testing high risk rule.

Now turning to FIGS. 22 and 23, the logic sequence for generation of a high risk monitor rule criteria is illustrated. The user enters the high risk editor and may edit an existing rule or add a new rule (or criteria). The criteria includes patient parameters such as, HbAlc, lipid CDL), Microalbumin, Liver Enzyme (ALT), Liver Enzyme (AST), Complication, Comorbidity, Risk Factor, BMI, BP, ER Visits, Days Hospitalized, Days Lost From Activities, SMBG Daily Min, and SMBG Daily Max. Next, the user is prompted with respect to whether the criteria is date deliminated or numeric deliminated (and/or both). If a test result, patients who have not been tested may be included. Referring now to FIG. 24, the logic sequence to generate a high risk rule for patients taking medication which may adversely impact the liver is illustrated. The FDA now recommends that liver enzyme testing be performed on patients taking specific medications. The user selects a medication category, is then prompted to determine if it is a new or existing medication and is then prompted to determine whether the medication is associated with an adverse reaction. If the medication is associated with a liver reaction, a high risk rule is generated to require testing for liver enzymes. If the enzyme is present, the action sequence is initiated (FIGS. 11A–11C).

While preferred embodiments have been shown and described, various modifications and substitutions may be made thereto without departing from the spirit and scope of the invention. Accordingly, it is to be understood that the present invention has been described by way of illustration and not by limitation.

What is claimed is:

1. A system for monitoring a chronic disease, comprising:
   a database for storing a plurality of patient data entries, each of said patient data entries including personal information of a patient and a guideline concerning the patient's care, said guideline including a default test value associated with monitoring said disease;
   a user interface for displaying said patient data entries stored in said database and entering patient entries for storage in said database; and
   a processor for retrieving patient data entries selected by said user interface from said data base and storing said patient data entries in accordance to an algorithm;
   wherein said processor further separates said patient entries designated by said user interface according to said default test values stored in said guideline.

2. A system, as defined in claim 1, wherein said algorithm comprises a plurality of rules for comparing said patient data entries to said default test value to determine whether said default test value has been crossed.

3. A system, as defined in claim 2, wherein said processor, in response to a patient data entry inputted by a user, compares said patient data entries to said default test value and categorizes a patient as a high risk patient if said default test value has been crossed.

4. A system, as defined in claim 3, further comprising an off site user interface which communicates with said processor.

5. A system, as defined in claim 3, wherein said processor generates an alert for a patient having a patient data entry crossing said default test value.

6. A system, as defined in claim 3, wherein said patient data entry comprises a test result data electronically transferred from a meter device to said processor for storage in said database.

7. A system, as defined in claim 2, wherein said patient data entry comprises test result data electronically transferred from a blood glucose monitor device to said processor for storage in said database.

8. A system, as defined in claim 2, wherein said patient data entry comprises a test result data electronically transferred from an external laboratory to said processor for storage in said database.

9. A system for monitoring a chronic disease, comprising:
   a database for storing a plurality of patient data entries, each of said patient data entries including personal information of a patient and a guideline concerning the patient's care, said guideline including a default test value associated with monitoring said disease;
   a user interface for displaying said patient data entries stored in said database and entering patient entries for storage in said database; and
   a processor for retrieving patient data entries selected by said user interface from said data base and storing said patient data entries in accordance to an algorithm;
   wherein said processor further separates said patient entries designated by said user interface according to a test threshold for HbAlc stored in said guideline.

10. A system for monitoring a chronic disease, comprising:
    a database for storing a plurality of patient data entries, each of said patient data entries including personal information of a patient and a guideline concerning the patient's care, said guideline including a default test value associated with monitoring said disease;
    a user interface for displaying said patient data entries stored in said database and entering patient entries for storage in said database; and
    a processor for retrieving patient data entries selected by said user interface from said data base and storing said patient data entries in accordance to an algorithm;
    wherein said processor further separates said patient entries designated by said user interface according to a test threshold for microalbumin stored in said guideline.

11. A system for monitoring a chronic disease, comprising:
    a database for storing a plurality of patient data entries, each of said patient data entries including personal information of a patient and a guideline concerning the patient's care, said guideline including a default test value associated with monitoring said disease;

a user interface for displaying said patient data entries stored in said database and entering patient entries for storage in said database; and a processor for retrieving patient data entries selected by said user interface from said data base and storing said patient data entries in accordance to an algorithm;

wherein said processor further separates said patient entries designated by said user interface according to a test threshold for lipids stored in said guideline.

12. A system for monitoring a chronic disease, comprising:

a database for storing a plurality of patient data entries, each of said patient data entries including personal information of a patient and a guideline concerning the patient's care, said guideline including a default test value associated with monitoring said disease;

a user interface for displaying said patient data entries stored in said database and entering patient entries for storage in said database; and a processor for retrieving patient data entries selected by said user interface from said data base and storing said patient data entries in accordance to an algorithm;

wherein said processor further separates said patient entries designated by said user interface according to a test threshold for liver enzymes stored in said guideline.

13. A system for monitoring a chronic disease, comprising:

a database for storing a plurality of patient data entries, each of said patient data entries including personal information of a patient and a guideline concerning the patient's care, said guideline including a default test value associated with monitoring said disease;

a user interface for displaying said patient data entries stored in said database and entering patient entries for storage in said database; and a processor for retrieving patient data entries selected by said user interface from said data base and storing said patient data entries in accordance to an algorithm;

wherein said patient entries further comprise clinical notations concerning whether a patient has received a scheduled service and said processor further separates said patient entries designated by said user interface according to whether a patient has achieved a clinical event.

14. A system, as defined in claim 2, wherein said patient data entry comprises test result data electronically transferred from a diagnostic monitoring device to said processor for storage in said database.

15. A system, as defined in claim 2, wherein said patient data entry comprises a test result data electronically transferred from a laboratory to said processor for storage in said database.

16. In a computer processing system, a method for monitoring a disease in a patient, comprising:

storing a treatment guideline defining at least one treatment step and a predetermined treatment monitoring threshold for the treatment step;

measuring a condition of the patient in accordance with the treatment step;

selectively comparing the measured condition to the treatment monitoring threshold;

if the measured condition exceeds the predetermined treatment monitoring threshold, generating a notification message; and generating periodic notification messages of at least one of scheduled treatment steps, measured conditions, missed treatment steps, and a trend in measured conditions.

17. The method as set forth in claim 16, wherein the periodic notification messages are transmitted to at least one of the patient, a physician, and a health care plan administrator.

18. In a computer processing system, a method for customizing treatment of a disease to a particular patient, comprising:

providing a treatment guideline for the disease defining treatment steps and predetermined treatment monitoring thresholds for respective treatment steps;

measuring a condition of the particular patient at corresponding treatment steps;

customizing the treatment guideline by at least one of adding, changing and deleting treatment steps in accordance with a measured condition;

storing the customized treatment guideline and measured conditions of the particular patient; and generating periodic notification messages of at least one of scheduled treatment steps, measured conditions, missed treatment steps, and a trend in measured conditions.

19. The method as set forth in claim 16, wherein the periodic notification messages are transmitted to a health care provider.

\* \* \* \* \*